United States Patent
Bonrath et al.

(10) Patent No.: US 9,561,989 B2
(45) Date of Patent: Feb. 7, 2017

(54) PROCESS OF ASYMMETRIC HYDROGENATION OF KETALS AND ACETALS

(71) Applicant: DSM IP ASSETS B.V., Heerlen (NL)

(72) Inventors: Werner Bonrath, Kaiseraugst (CH); Thomas Netscher, Kaiseraugst (CH); Jonathan Alan Medlock, Kaiseraugst (CH); Gerardus Karel Maria Verzijl, Kaiseraugst (CH); Andreas Hendrikus Maria De Vries, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/652,562

(22) PCT Filed: Dec. 18, 2013

(86) PCT No.: PCT/EP2013/077231
§ 371 (c)(1),
(2) Date: Jun. 16, 2015

(87) PCT Pub. No.: WO2014/096096
PCT Pub. Date: Jun. 26, 2014

(65) Prior Publication Data
US 2016/0185683 A1 Jun. 30, 2016

(30) Foreign Application Priority Data
Dec. 18, 2012 (EP) .................................... 12197861

(51) Int. Cl.
| | | |
|---|---|---|
| *C07D 507/02* | (2006.01) |
| *C07B 35/02* | (2006.01) |
| *C07D 317/12* | (2006.01) |
| *C07C 41/48* | (2006.01) |
| *C07B 53/00* | (2006.01) |
| *C07D 311/72* | (2006.01) |
| *C07D 319/06* | (2006.01) |
| *B01J 31/18* | (2006.01) |
| *C07C 41/56* | (2006.01) |
| *C07C 41/58* | (2006.01) |

(52) U.S. Cl.
CPC .............. *C07B 35/02* (2013.01); *B01J 31/189* (2013.01); *C07B 53/00* (2013.01); *C07C 41/48* (2013.01); *C07C 41/56* (2013.01); *C07C 41/58* (2013.01); *C07D 311/72* (2013.01); *C07D 317/12* (2013.01); *C07D 319/06* (2013.01); *B01J 2231/34* (2013.01); *B01J 2531/827* (2013.01); *C07B 2200/07* (2013.01); *C07B 2200/09* (2013.01)

(58) Field of Classification Search
None
See application file for complete search history.

(56) References Cited

FOREIGN PATENT DOCUMENTS

| | | | | |
|---|---|---|---|---|
| CH | WO 2006066863 A1 * | 6/2006 | ............. | C07B 53/00 |
| CN | 101087774 | 12/2007 | | |
| EP | 0 565 975 | 10/1993 | | |
| EP | 2 275 398 | 1/2011 | | |
| WO | WO 2006/066863 | 6/2006 | | |

OTHER PUBLICATIONS

Smidt, S. et al., Chem. Eur J. 2004, vol. 10, pp. 4685-4693.*
International Search Report for PCT/EP2013/077231 mailed Jan. 22, 2014, four pages.
Smidt et al., "Enantioselective Hydrogenation of alkenes with Iridium-Phox Catalysts: A Kinetic Study of Anion Effects", *Chemistry—A European Journal*, vol. 10, No. 19, Jan. 1, 2004, pp. 4685-4693.
Jian-Hua et al., "An Additional Coordination Group Leads to Extremely Efficient Chiral Iridium Catalysts for Assymetric Hydrogenation of Ketones", *Angewandte Chemie International Edition*, vol. 50, No. 32, Aug. 1, 2011, pp. 7329-7332.
Official Action, CN Application No. 201380065931.3, Mar. 21, 2016.

* cited by examiner

*Primary Examiner* — Heidi Reese
(74) *Attorney, Agent, or Firm* — Nixon & Vanderhye P.C.

(57) ABSTRACT

The present invention relates to a process of the asymmetric hydrogenation of a ketal of an unsaturated ketone or an acetal of an unsaturated aldehyde by molecular hydrogen in the presence of at least one chiral iridium complex. This process yields chiral compounds in a very efficient way and is very advantageous in that the amount of iridium complex can be remarkably reduced.

25 Claims, No Drawings

PROCESS OF ASYMMETRIC HYDROGENATION OF KETALS AND ACETALS

This application is the U.S. national phase of International Application No. PCT/EP2013/077231 filed 18 Dec. 2013 which designated the U.S. and claims priority to EP 12197861.3 filed 18 Dec. 2012, the entire contents of each of which are hereby incorporated by reference.

TECHNICAL FIELD

The present invention relates to the field of asymmetric hydrogenations of unsaturated compounds.

BACKGROUND OF THE INVENTION

Chiral compounds are important products and intermediates in different fields of application, particularly in the field of pharma, food supplements and flavours and fragrances as different stereoisomers have strongly different properties. A very important class of chiral compounds are chiral ketones and aldehydes.

Particularly important are chiral ketones for the synthesis of aroma ingredients and for vitamins, particular for tocopherol and vitamin K1.

Natural tocopherols bear a side chain having 3 stereogenic centres of the R configuration. Synthetic routes for the synthesis of (2R,4'R,8'R)-α-tocopherol are possible starting from (R,R)-isophytol or (R,R)-phytol. However, as natural sources of (2R,4'R,8'R)-tocopherols and (R,R)-phytol, are very limited, the market has a strong need for an effective synthesis of (2R,4'R,8'R)-tocopherols and (R,R)-isophytol, respectively, and chiral ketones or aldehydes are important intermediates for their synthesis.

It is known that chiral ketones are accessible from asymmetric hydrogenation of unsaturated ketones using chiral transition metal complexes. An important class of chiral transition metal complexes are chiral iridium complexes.

For example WO 2006/066863 A1 discloses a specific class of chiral iridium complexes which are suitable for the asymmetric hydrogenation of alkenes showing high stereoselectivity in the formation of hydrogenated ketones at high conversion. However, the iridium complexes need to be used in a relatively high amount relative to the unsaturated compounds to be hydrogenated. Due to the high price of iridium complexes it is commercially interesting to use as little iridium complex as possible while maintaining high conversion and good stereoselectivity.

SUMMARY OF THE INVENTION

Therefore, the problem to be solved is to offer a system for increasing the efficiency of iridium complexes in an asymmetric hydrogenation by molecular hydrogen.

Surprisingly it has been found that this problem can be solved by a process according to claim 1 or 14 or a composition according to claim 15.

This processes lead to the possibility that significantly lower amounts of chiral iridium complex can be used as compared to the known methods and whilst still obtaining the high conversion and high stereoselectivity.

It has been further found that the combination with specific additives and/or halogenated solvents improves the efficiency of the chiral iridium complexes even significantly further.

Further aspects of the invention are subject of further independent claims. Particularly preferred embodiments are subject of dependent claims.

DETAILED DESCRIPTION OF THE INVENTION

In a first aspect the present invention relates to a process of asymmetric hydrogenation of a ketal of an unsaturated ketone or an acetal of an unsaturated aldehyde by molecular hydrogen in the presence of at least one chiral iridium complex to yield a ketal or acetal having at least one stereogenic carbon centre.

The term "independently from each other" in this document means, in the context of substituents, moieties, or groups, that identically designated substituents, moieties, or groups can occur simultaneously with a different meaning in the same molecule.

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH(CH$_3$)—CH$_2$—CH$_3$ is considered as a $C_4$-alkyl group.

A "$C_{x-y}$-alkylene" group is an alkylene group comprising x to y carbon atoms, i.e., for example $C_2$-$C_6$ alkylene group is an alkyl group comprising 2 to 6 carbon atoms. The alkylene group can be linear or branched. For example the group —CH(CH$_3$)—CH$_2$— is considered as a $C_3$-alkylene group.

A "phenolic alcohol" means in this document an alcohol which has a hydroxyl group which is bound directly to an aromatic group.

The term "(R,R)-isophytol" used in this document means (3RS,7R,11R)-3,7,11,15-tetramethylhexadec-1-en-3-ol).

The term "(R,R)-phytol" used in this document means (2E,7R,11R)-3,7,11,15-tetramethyl-2-hexadecen-1-ol).

Substance names starting with "poly" as used in the present document refer to substances formally containing two or more of the corresponding functional groups per molecule.

The term "stereogenic centre" as used in this document is an atom, bearing groups such that an interchanging of any two of the groups leads to a stereoisomer. Stereoisomers are isomeric molecules that have the same molecular formula and sequence of bonded atoms (constitution), but that differ in the three-dimensional orientations of their atoms in space.

The configuration at a stereogenic centre is defined to be either R or S. The R/S-concept and rules for the determination of the absolute configuration in stereochemistry is known to the person skilled in the art.

In the present document any single dotted line represents the bond by which a substituent is bound to the rest of a molecule.

Cis/trans isomers are configurational isomers having different orientation at the double bond. In this document the term "cis" is equivalently used for "Z" and vice versa as well as "trans" for "E" and vice versa. Therefore, for example the term "cis/trans isomerization catalyst" is equivalent to the term "E/Z isomerization catalyst".

A "cis/trans isomerization catalyst" is a catalyst which is able to isomerize a cis isomer (Z-isomer) to a cis/trans isomer mixture (E/Z isomer mixture) or to isomerize a trans isomer (E-isomer) to a cis/trans isomer (E/Z isomer mixture).

The terms "E/Z", "cis/trans" and "R/S" denote mixtures of E and Z, of cis and trans, and of R and S, respectively.

The term "isomerization" or "isomerize" is to be understood as being limited to cis/trans isomerization in the whole document.

A "completely saturated" ketone, aldehyde, acetal or ketal is an unsaturated ketone, aldehyde, acetal or ketal in which all carbon-carbon double bonds have been hydrogenated by asymmetric hydrogenation.

An "unsaturated ketone" or "unsaturated aldehyde" in this document ketone is defined as to be a ketone or aldehyde which is olefinically unsaturated, i.e. that it has at least one carbon-carbon double bond in its chemical structure, and which has at least one prochiral carbon-carbon double bond.

"Assay yield" of an asymmetric hydrogenation is in the present application the molar ratio of number of molecules of completely saturated ketones or aldehydes or ketals or acetals to the number of molecules of unsaturated ketones or aldehydes or ketals or acetals being submitted to the hydrogenation.

In case identical labels for symbols or groups are found in several formulae, in the present document, the definition of said group or symbol made in the context of one specific formula applies also to other formulae which comprises said same label.

Unsaturated Ketone or Aldehyde

The unsaturated aldehyde or unsaturated ketone has at least one carbon-carbon double bond in its chemical structure and has at least one prochiral carbon-carbon double bond.

In one embodiment, the unsaturated ketone or unsaturated aldehyde is a ketone or an aldehyde having a carbon-carbon double bond in the α,β-position to the C=O group.

In another embodiment, the unsaturated ketone or unsaturated aldehyde is a ketone or an aldehyde having a carbon-carbon double bond in the γ,δ-position to the C=O group.

It can be that the unsaturated ketone or the unsaturated aldehyde has a carbon-carbon double bond in the α,β-position as well as a carbon-carbon double bond in the γ,δ-position to the C=O group.

In case the unsaturated ketone or unsaturated aldehyde or the ketal or acetal thereof has more than one prochiral carbon-carbon double bonds such compounds may have the same ("all Z" or "all E") E/Z configurations or have different E/Z configurations (e.g. EZ or ZE). For the purpose of this invention, it is advisable that only those isomers having the E-configuration at all prochiral carbon-carbon double bonds and those isomers having the Z-configuration at all prochiral carbon-carbon double bond are submitted to the asymmetric hydrogenation. It is preferred that having in the same molecule different E/Z configurations at the prochiral carbon-carbon double bonds are submitted to a step of cis/trans isomerization of said prochiral carbon-carbon double bonds. Such a cis/trans isomerization is performed in the presence of a cis/trans isomerization catalyst, particularly an organic sulphur compound, particularly a polythiol, or nitrogen monoxide. This allows that undesired isomers are converted into such isomers having all E or all Z configuration at the corresponding prochiral double bonds.

Preferably, the unsaturated ketone or unsaturated aldehyde has the formula (I) or (II)

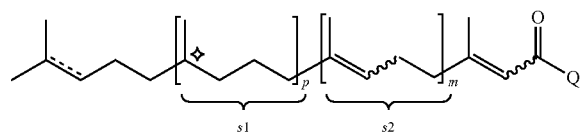

(I)

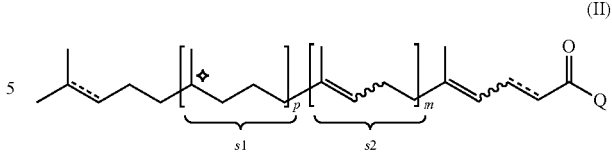

(II)

wherein Q stands for H or $CH_3$ and m and p stand independently from each other for a value of 3 with the proviso that the sum of m and p is 0 to 3, and where a wavy line represents a carbon-carbon bond which is linked to the adjacent carbon-carbon double bond so as to have said carbon-carbon double bond either in the Z or in the E-configuration and where the substructures in formula (I) and (II) represented by s1 and s2 can be in any sequence;

and wherein the double bond having dotted lines ( === ) in formula (I) and (II) represent either a single carbon-carbon bond or a double carbon-carbon bond;

and wherein ✧ represents a stereogenic centre.

The sum of m and p is preferably 0 to 2, particularly 0 or 1.

The unsaturated ketone or unsaturated aldehyde of formula (I) or (II), hence, can be an individual substance or a mixture of different stereoisomers having different orientation at the stereogenic centres marked by ✧ or at the double bond to which the wavy bond is attached. It is preferred, however, that the unsaturated ketone or unsaturated aldehyde of formula (I) or (II) is a single stereoisomer with specific configuration(s) at the stereogenic centres and double bonds. It is preferred that the configuration at the stereogenic centre(s) is the R-configuration. In case of p≥2, it is preferred that all the different stereogenic centres marked by ✧ in have the same configuration, i.e. all the S-configuration or all the R-configuration, preferably all in the R-configuration.

Particularly preferred is the unsaturated ketone or unsaturated aldehyde has the formula (II), particularly being selected from the group consisting of 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Most preferably the unsaturated ketone or unsaturated aldehyde has the formula (II) is selected from the group consisting of 3,7-dimethyloct-6-enal, 3,7-dimethylocta-2,6-dienal, 3,7-dimethyloct-2-enal, 6,10-dimethylundeca-3,5,9-trien-2-one, 6,10-dimethylundeca-5,9-dien-2-one, 6,10-dimethylundec-5-en-2-one, 6,10-dimethylundec-3-en-2-one, 6,10-dimethylundec-3,5-diene-2-one, 6,10,14-trimethylpentadeca-5,9,13-trien-2-one, 6,10,14-trimethylpentadeca-5,9-dien-2-one, 6,10,14-trimethylpentadec-5-en-2-one and (R)-6,10,14-trimethylpentadec-5-en-2-one as well as all their possible E/Z-isomers.

Ketal or Acetal of an Unsaturated Ketone or Aldehyde

The formation of a ketal from a ketone, or of an acetal from an aldehyde, per se, is known to the person skilled in the art.

The ketal of an unsaturated ketone can be preferably formed from the above mentioned unsaturated ketone and an alcohol. The acetal of an unsaturated aldehyde can be preferably formed from the above mentioned unsaturated aldehyde and an alcohol.

It is known to the person skilled in the art that there are alternative routes of synthesis for acetal or ketals. In principle, the ketal and acetals can also be formed by treating a ketone or an aldehyde with ortho-esters or by trans-ketalization such as disclosed for example in Pério et al., *Tetrahedron Letters*, Vol. 38, 45, 7867-7870, 1997 or in Lorette, *J. Org. Chem.* 1960, 521-525, the entire content of both is hereby incorporated by reference.

Hence, the ketal or the acetal is preferably formed from an unsaturated ketone or an acetal of an unsaturated aldehyde and an alcohol or by treating a ketone or an aldehyde with ortho-esters or by trans-ketalization or by trans-acetalization.

Preferably the ketal or acetal is formed from the above mentioned unsaturated ketone or unsaturated aldehyde, particularly form a unsaturated ketone or unsaturated aldehyde of formula (I) or (II), and an alcohol.

The alcohol used for the ketal or acetal formation can, principally, be any alcohol, i.e. the alcohol may comprise one or more hydroxyl groups. The alcohol may be a phenolic alcohol or an aliphatic or cycloaliphatic alcohol.

Preferably, however, the alcohol has one hydroxyl groups (=monol) or two hydroxyl groups (=diol).

In case the alcohol has one hydroxyl group, the alcohol is preferably an alcohol which has 1 to 12 carbon atoms. Particularly, the alcohol having one hydroxyl group is selected from the group consisting of methanol, ethanol, 1-propanol, 2-propanol, 1-butanol, 2-methyl-1-propanol, 2-butanol, pentane-1-ol, 3-methylbutane-1-ol, 2-methylbutane-1-ol, 2,2-dimethylpropan-1-ol, pentane-3-ol, pentane-2-ol, 3-methylbutane-2-ol, 2-methylbutan-2-ol, hexane-1-ol, hexane-2-ol, hexane-3-ol, 2-methyl-1-pentanol, 3-methyl-1-pentanol, 4-methyl-1-pentanol, 3-methyl-2-pentanol, 4-methyl-2-pentanol, 2-methyl-3-pentanol, 2,2-dimethyl-1-butanol, 2,3-dimethyl-1-butanol, 3,3-dimethyl-1-butanol, 3,3-dimethyl-2-butanol, 2-ethyl-1-butanol, and all structural isomers of heptanol, octanol and halogenated $C_1$-$C_8$-alkyl alcohols, particularly 2,2,2-trifluoroethanol. Particularly suitable are primary or secondary alcohols. Preferably primary alcohols are used as alcohols with one hydroxyl group. Particularly methanol, ethanol, 1-propanol, 2-propanol, 1-butanol, 2-butanol or 2,2,2-trifluoroethanol, preferably methanol, ethanol, 1-propanol, 1-butanol or 2,2,2-trifluoroethanol, are used as alcohols with one hydroxyl group.

In another embodiment the alcohol is a diol, hence has two hydroxyl groups. Preferably the diol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2,2-dimethylpropane-1,3-diol, 1,2-dimethylpropane-1,3-diol, benzene-1,2-diol and cyclohexane-1,2-diols. From two cyclohexane-1,2-diols the preferred stereoisomer is syn-cyclohexane-1,2-diol (=cis-cyclohexane-1,2-diol).

The two hydroxyl group are in one embodiment bound to two adjacent carbon atoms, hence these diols are vicinal diols. Vicinal diols form a 5 membered ring in a ketal or acetal.

Particularly suitable are vicinal diols which are selected from the group consisting of ethane-1,2-diol, propane-1,2-diol, butane-1,2-diol, butane-2,3-diol, 2-methylpropane-1,2-diol, benzene-1,2-diol and syn-cyclohexane-1,2-diol, particularly ethane-1,2-diol.

Other particularly suitable are diols, in which the hydroxyl groups are separated by 3 carbon atoms, and, hence, form a very stable 6 membered ring in a ketal or acetal. Particularly suitable diols of this type are propane-1,3-diol, butane-1,3-diol, 2-methylpropane-1,3-diol, 2-methylbutane-1,3-diol, 2,2-dimethylpropane-1,3-diol, 1,2-dimethylpropane-1,3-diol, 3-methylpentane-2,4-diol and 2-(hydroxymethyl)cyclohexanol.

Preferably primary alcohols are used as diols.

Particularly suitable the are alcohol is a halogenated $C_1$-$C_8$-alkyl alcohol, preferably 2,2,2-trifluoroethanol, or a diol which is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)cyclohexanol, benzene-1,2-diol and cyclohexane-1,2-diols.

The reaction conditions and stoichiometry used for the acetal or ketal formation are known to the person skilled in the art. Particularly the acetal or ketal is formed under the influence of an acid.

The preferred ketal of an unsaturated ketone or the preferred acetal of an unsaturated aldehyde are of formula (XI) or (XII)

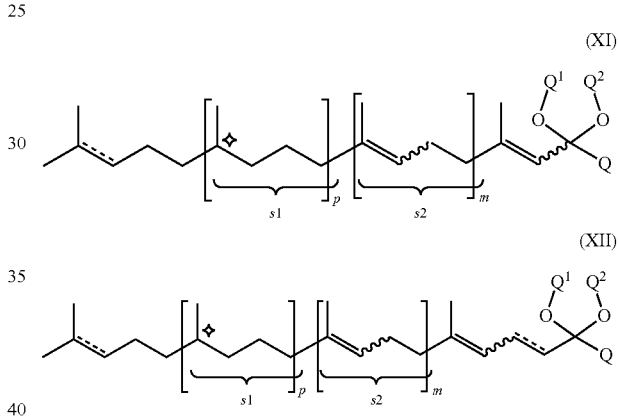

The groups and symbols in formula (XI) and (XII) have the same meaning as defined before for formula (I) and (II).

$Q^1$ and $Q^2$ stand either individually both or for a $C_1$-$C_{10}$ alkyl group or a halogenated $C_1$-$C_{10}$ alkyl group;

or form together a $C_2$-$C_6$ alkylene group or a $C_6$-$C_8$ cycloalkylene group.

$Q^1$ and $Q^2$ stand particularly for either a linear $C_1$-$C_{10}$ alkyl group or fluorinated linear $C_1$-$C_{10}$ alkyl group, preferably a linear $C_1$-$C_4$ alkyl group or a —$CH_2CF_3$ group or a group of formula

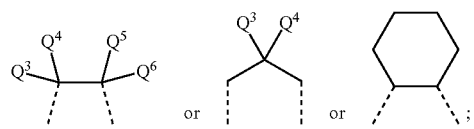

in which $Q^3$, $Q^4$, $Q^5$ and $Q^6$ are independently from each other hydrogen atoms or methyl groups.

Preferably the ketal or the acetal of formula (XI) or (XII) are (E)-2-(4,8-dimethylnona-3,7-dien-1-yl)-2,5,5-trimethyl-1,3-dioxane, (E)-2,6-dimethyl-10,10-bis(2,2,2-trifluoroethoxy)undeca-2,6-diene, (E)-2-(4,8-dimethylnon-3-en-1-yl)-2,5,5-trimethyl-1,3-dioxane, (E)-6,10-dimethyl-2,2-bis(2,2, 2-trifluoroethoxy)undec-5-ene, (E)-2,5,5-trimethyl-2-(4,8,12-trimethyltridec-3-en-1-yl)-1,3-dioxane, (R,E)-2,5,5-trimethyl-2-(4,8,12-trimethyltridec-3-en-1-yl)-1,3-dioxane, (E)-6,10,14-trimethyl-2,2-bis(2,2,2-trifluoroethoxy)pentadec-5-ene, (R,E)-6,10,14-trimethyl-2,2-bis(2,2,2-trifluoroethoxy)pentadec-5-ene, (Z)-2-(4,8-dimethylnona-3,7-dien-1-yl)-2,5,5-trimethyl-1,3-dioxane, (Z)-2,6-dimethyl-10,10-bis(2,2,2-trifluoro-ethoxy)undeca-2,6-diene, (Z)-2-(4,8-dimethylnon-3-en-1-yl)-2,5,5-trimethyl-1,3-dioxane, (Z)-6,10-dimethyl-2,2-bis(2,2,2-trifluoroethoxy)undec-5-ene, (Z)-2,5,5-trimethyl-2-(4,8,12-trimethyltridec-3-en-1-yl)-1,3-dioxane, (R,Z)-2,5,5-trimethyl-2-(4,8,12-trimethyltridec-3-en-1-yl)-1,3-dioxane, 2,5,5-trimethyl-2-((3E,7E)-4,8,12-trimethyltrideca-3,7,11-trien-1-yl)-1,3-dioxane, (6E,10E)-2,6,10-trimethyl-14,14-bis(2,2,2-trifluoroethoxy)pentadeca-2,6,10-triene, 2,5,5-trimethyl-2-((3E,7E)-4,8,12-trimethyltrideca-3,7-dien-1-yl)-1,3-dioxane, (5E,9E)-6,10,14-trimethyl-2,2-bis(2,2,2-trifluoroethoxy)pentadeca-5,9-diene, 2,5,5-trimethyl-2-((3Z,7E)-4,8,12-trimethyltrideca-3,7,11-trien-1-yl)-1,3-dioxane, 2,5,5-trimethyl-2-((3E,7Z)-4,8,12-trimethyltrideca-3,7,11-trien-1-yl)-1,3-dioxane, 2,5,5-trimethyl-2-((3Z,7Z)-4,8,12-trimethyltrideca-3,7,11-trien-1-yl)-1,3-dioxane, (6Z,10E)-2,6,10-trimethyl-14,14-bis(2,2,2-trifluoroethoxy)pentadeca-2,6,10-triene, (6E,10Z)-2,6,10-trimethyl-14,14-bis(2,2,2-trifluoroethoxy)pentadeca-2,6,10-triene, (6Z,10Z)-2,6,10-trimethyl-14,14-bis(2,2,2-trifluoroethoxy)pentadeca-2,6,10-triene, 2,5,5-trimethyl-2-((3Z,7E)-4,8,12-trimethyltrideca-3,7-dien-1-yl)-1,3-dioxane, 2,5,5-trimethyl-2-((3E,7Z)-4,8,12-trimethyltrideca-3,7-dien-1-yl)-1,3-dioxane, 2,5,5-trimethyl-2-((3Z,7Z)-4,8,12-trimethyltrideca-3,7-dien-1-yl)-1,3-dioxane, (5Z,9E)-6,10,14-trimethyl-2,2-bis(2,2,2-trifluoroethoxy)pentadeca-5,9-diene, (5E,9Z)-6,10,14-trimethyl-2,2-bis(2,2,2-trifluoroethoxy)pentadeca-5,9-diene, (5Z,9Z)-6,10,14-trimethyl-2,2-bis(2,2,2-trifluoroethoxy)pentadeca-5,9-diene, (E)-2-(2,6-dimethylhept-1-en-1-yl)-5,5-dimethyl-1,3-dioxane, (E)-3,7-dimethyl-1,1-bis(2,2,2-trifluoroethoxy)oct-2-ene, (E)-3,7-dimethyl-1,1-bis(2,2,2-trifluoroethoxy)octa-2,6-diene, (Z)-2-(2,6-dimethylhept-1-en-1-yl)-5,5-dimethyl-1,3-dioxane, (Z)-3,7-dimethyl-1,1-bis(2,2,2-trifluoroethoxy)oct-2-ene, (Z)-3,7-dimethyl-1,1-bis(2,2,2-trifluoroethoxy)octa-2,6-diene, 2,6-dimethyl-8,8-bis(2,2,2-trifluoroethoxy)oct-2-ene, (R)-2,6-dimethyl-8,8-bis(2,2,2-trifluoroethoxy)oct-2-ene, 2-((1 Z,3E)-4,8-dimethylnona-1,3,7-trien-1-yl)-2,5,5-trimethyl-1,3-dioxane, 2-((1E,3Z)-4,8-dimethylnona-1,3,7-trien-1-yl)-2,5,5-trimethyl-1,3-dioxane, 2-((1 Z,3Z)-4,8-dimethylnona-1,3,7-trien-1-yl)-2,5,5-trimethyl-1,3-dioxane, (6Z,8E)-2,6-dimethyl-10,10-bis(2,2,2-trifluoroethoxy)undeca-2,6,8-triene, (6E,8Z)-2,6-dimethyl-10,10-bis(2,2,2-trifluoroethoxy)undeca-2,6,8-triene, (6Z,8Z)-2,6-dimethyl-10,10-bis(2,2,2-trifluoroethoxy)undeca-2,6,8-triene, (Z)-2,5-dimethyl-2-(4,8,12-trimethyltridec-3-en-1-yl)-1,3-dioxane, (R,Z)-2,5-dimethyl-2-(4,8,12-trimethyltridec-3-en-1-yl)-1,3-dioxane, (Z)-6,10,14-trimethyl-2,2-bis(2,2,2-trifluoroethoxy)pentadec-5-ene, (R,Z)-6,10,14-trimethyl-2,2-bis(2,2,2-trifluoroethoxy)pentadec-5-ene, 2-methyl-2-((3E,7E)-4,8,12-trimethyltrideca-3,7-dien-1-yl)-1,3-dioxolane, 2-methyl-2-((3Z,7Z)-4,8,12-trimethyltrideca-3,7-dien-1-yl)-1,3-dioxolane, 2-methyl-2-((3E,E)-4,8,12-trimethyltrideca-3,7,11-trien-1-yl)-1,3-dioxolane, 2-methyl-2-((3Z,7Z)-4,8,12-trimethyltrideca-3,7,11-trien-1-yl)-1,3-dioxolane and (Z)-2-(4,8-dimethylnon-3-en-1-yl)-2-methyl-1,3-dioxolane.

Asymmetric Hydrogenation

The asymmetric hydrogenation of a ketal of an unsaturated ketone or an acetal of an unsaturated aldehyde is done by molecular hydrogen in the presence of at least one chiral iridium complex.

Chiral iridium complexes are compounds having organic ligands being coordinated to a central iridium atom. The chirality of chiral iridium complexes is due to either the chirality of the ligands or the spacial arrangements of the ligands. This concept of chirality is well known from complex chemistry. Ligands can be monodentate or polydentate. Preferably, the ligands bound to the iridium central atom are chelating ligands.

For the present invention, it has been shown that particularly chiral iridium complexes having ligands bound to the iridium central atom and that exactly one of the ligands is an organic ligand bearing a stereogenic centre, particularly a chelating ligand bearing a stereogenic centre, are very suitable.

It is preferred that the chiral iridium complex is bound to a chelating organic ligand having N and P as coordinating atoms and to either two olefins or to a diene having two carbon-carbon double bonds, and that, hence, the chiral iridium complex has preferably the following formula (III-0)

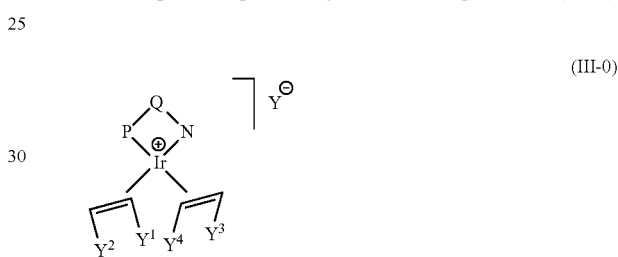

wherein

P-Q-N stands for a chelating organic ligand comprising a stereogenic centre or has planar or axial chirality and has a nitrogen and phosphorous atom as binding site to the iridium centre of the complex;

$Y^1$, $Y^2$, $Y^3$ and $Y^4$ are independently from each other hydrogen atoms, $C_{1-12}$-alkyl, $C_{5-10}$-cycloalkyl, or aromatic group; or at least two of them form together at least a two-valent bridged group of at least 2 carbon atoms; and $Y^\ominus$ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C-SO_3^-$ or $F_9C_4-SO_3^-$; $ClO_4^-$, $Al(OC_6F_5)_4^-$, $Al(OC(CF_3)_3)_4^-$, $N(SO_2CF_3)_2^- N(SO_2C_4F_9)_2^-$ and $B(C_6F_5)_4^-$.

The nitrogen and the phosphorous atom are preferably separated by 2 to 5, preferably 3, atoms in the chemical formula of the ligand P-Q-N.

The chelating organic ligand P-Q-N is preferably selected from the formulae (III-N1), (III-N2), (III-N3), (III-N4), (III-N5), (III-N6), (III-N7), (III-N8) and (III-N9)

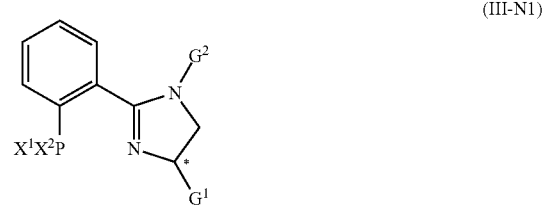

-continued

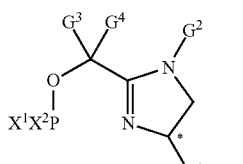
(III-N2)

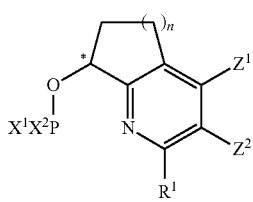
(III-N3)

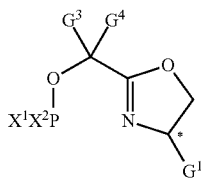
(III-N4)

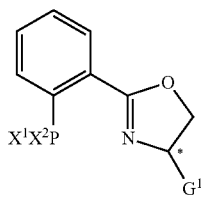
(III-N5)

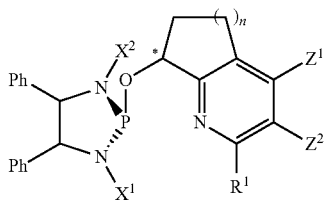
(III-N6)

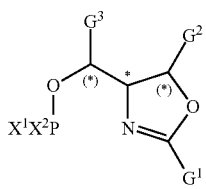
(III-N7)

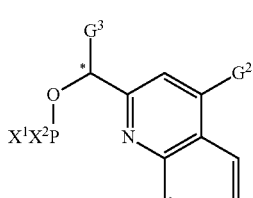
(III-N8)

-continued

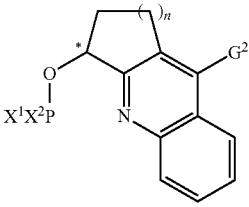
(III-N9)

wherein $G^1$ represents either a $C_1$-$C_4$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl group;

$G^2$, $G^3$ and $G^4$ represent independently from each other hydrogen atoms or a $C_1$-$C_4$-alkyl, $C_{5-7}$-cycloalkyl, adamantyl, phenyl (optionally substituted with one to three $C_{1-5}$-, $C_{1-4}$-alkoxy, $C_{1-4}$-perfluoroalkyl groups and/or one to five halogen atoms)), benzyl, 1-naphthyl, 2-naphthyl, 2-furyl group;

$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-alkyl, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;

Ph stands for phenyl;

n is 1 or 2 or 3, preferred 1 or 2;

and $R^1$, $Z^1$ and $Z^2$ are as defined later for formula (III)

In case $Y^1$ and $Y^2$ and/or $Y^3$ and $Y^4$ form an olefin of the formula $Y^1$══$Y^2$ and/or of the Formula $Y^3$══$Y^4$, this olefin is or these olefins are preferably selected from the group consisting of ethene, prop-1-ene, 2-methylprop-1-ene, 2-methylbut-2-ene, 2,3-dimethylbut-2-ene, (Z)-cyclooctene, cyclohexene, cyclo-heptene, cyclopentene and norbornene.

In case $Y^1$, $Y^2$, $Y^3$ and $Y^4$ are forming a diene, it is either cyclic (double bond in a cycle) or acyclic (double bond not in a cycle).

The two carbon-carbon double bonds of the diene are preferably linked by two carbon bonds, i.e. the dienes preferably comprise the substructure C══C—C—C—C══C.

Examples of preferred acylic dienes are hexa-1,5-diene, hepta-1,5-diene, octa-1,5-diene, octa-2,6-diene, 2,4-dialkyl-2,7-octadiene, 3,6-dialkylocta-2,6-diene, 1,2-divinylcyclohexane and 1,3-butadiene.

Examples for cyclic dienes are cycloocta-1,5-diene, cyclohexa-1,4-diene, cyclohexa-1,3-diene, 3,4,7,8-tetraalkylcycloocta-1,5-diene, 3,4,7-trialkylcycloocta-1,5-diene, 3,4-di-alkylcycloocta-1,5-diene, 3,7-di-alkylcycloocta-1,5-diene, 3,8-di-alkylcycloocta-1,5-diene, 3-alkylcycloocta-1,5-diene; norbornadiene, 1-alkylnorbornadiene, 2-alkylnorbornadiene, 7-alkylnorbornadiene, dicyclopentadiene, cyclo-pentadiene and (1s,4s)-bicyclo[2.2.2]octa-2,5-diene.

Preferred diene is cycloocta-1,5-diene.

A highly preferred class of chiral iridium complexes are chiral iridium complexes of formula (III)

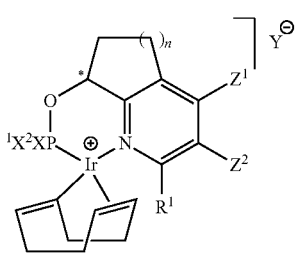

(III)

wherein
n is 1 or 2 or 3, preferred 1 or 2;
$X^1$ and $X^2$ are independently from each other hydrogen atoms, $C_{1-4}$-alkyl, $C_{5-7}$-cycloalkyl, adamantyl, phenyl (optionally substituted with one to three $C_{1-5}$-, $C_{1-4}$-alkoxy, $C_{1-4}$-perfluoroalkyl groups and/or one to five halogen atoms)), benzyl, 1-naphthyl, 2-naphthyl, 2-furyl or ferrocenyl;
$Z^1$ and $Z^2$ are independently from each other hydrogen atoms, $C_{1-5}$-alkyl or $C_{1-5}$-alkoxy groups;
or $Z^1$ and $Z^2$ stand together for a bridging group forming a 5 to 6 membered ring;
$Y^{\ominus}$ is an anion, particularly selected from the group consisting of halide, $PF_6^-$, $SbF_6^-$, tetra(3,5-bis(trifluoromethyl)phenyl)borate ($BAr_F^-$), $BF_4^-$, perfluorinated sulfonates, preferably $F_3C$—$SO_3^-$ or $F_9C_4$—$SO_3^-$; $ClO_4^-$, $Al(OC_6F_5)_4^-$, $Al(OC(CF_3)_3)_4^-$, $N(SO_2CF_3)_2^-$ $N(SO_2C_4F_9)_2^-$ and $B(C_6F_5)_4^-$;
$R^1$ represents either phenyl or o-tolyl or m-tolyl or p-tolyl or a group of formula (IVa) or (IVb) or (IVc)

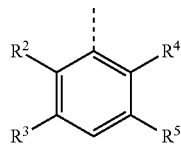

(IVa)

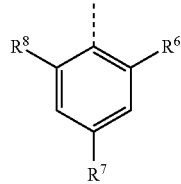

(IVb)

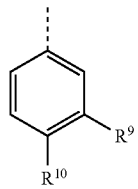

(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogen atoms or by $C_1$-$C_4$-alkyl groups or by $C_1$-$C_4$-alkoxy groups
$R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;
$R^6$ and $R^7$ and $R^8$ represent each a $C_1$-$C_4$-alkyl group or a halogenated $C_1$-$C_4$-alkyl group;
$R^9$ and $R^{10}$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;
and wherein * represents a stereogenic centre of the complex of formula (III).

The complex of formula (III) is neutral, i.e. the complex consists of a complex cation of formula (III') and anion Y as defined before.

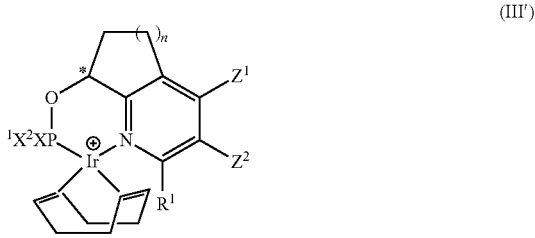

(III')

The person skilled in the art knows that anions and cations may be dissociated.

$X^1$ and/or $X^2$ represent preferably hydrogen atoms, methyl, ethyl, n-propyl, iso-propyl, n-butyl, iso-butyl, tert-butyl, n-pentyl, iso-pentyl, neopentyl, cyclopentyl, cyclohexyl, cycloheptyl, adamantly, phenyl, benzyl, o-tolyl, m-tolyl, p-tolyl, 4-methoxyphenyl, 4-trifluoromethylphenyl, 3,5-di-tert-butylphenyl, 3,5-dimethoxyphenyl, 1-naphthyl, naphthyl, 2-furyl, ferrocenyl or a phenyl group which is substituted with one to five halogen atoms.

In case of $X^1$ and/or $X^2$ representing phenyl groups which are substituted with one to five halogen atoms, the phenyl groups substituted by fluorine atoms are particularly useful, i.e. $C_6H_4F$, $C_5H_3F_2$, $C_5H_2F_3$, $C_5HF_4$ or $C_5F_5$.

In case of $X^1$ and/or $X^2$ representing phenyl groups which are substituted with one to three $C_{1-4}$-alkyl, the phenyl groups substituted by methyl group(s) are particularly useful, particularly ortho-tolyl and para-tolyl.

Preferably both $X^1$ and $X^2$ represent the same substituent.

Most preferred both $X^1$ and $X^2$ are phenyl or ortho-tolyl groups.

It is preferred that the $C_1$-$C_4$-alkyl or alkoxy groups used in the definition of $R^2$, $R^3$, $R^4$, $R^5$, $R^6$, $R^7$, $R^8$, $R^9$ and $R^{10}$ above are primary or secondary, preferably primary, alkyl or alkoxy groups.

A particularly suited substituent $R^1$ of formula (IVa) is the 9-anthryl or 1-naphthyl group.

A further particularly suited substituent $R^1$ of formula (IVb) is the mesityl group.

A further particularly suited substituent $R^1$ of formula (IVc) is the 2-naphthyl group.

Preferably $R^1$ is represented by phenyl (abbreviated as "Ph") or formula (IV-1) or (IV-2) or (IV-3), particularly (IV-1) or (IV-3).

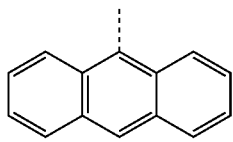
(IV-1)

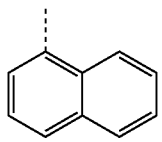
(IV-2)

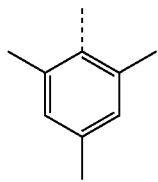
(IV-3)

abbreviated as "Anth"  abbreviated as "1-Naphth"  abbreviated as "Mes"

It has been found that the most preferred substituent $R^1$ is either 9-anthryl or phenyl.

The preferred chiral iridium complexes of formula (III) are the complexes of formulae (III-A), (III-B), (III-C), (III-D), (III-E) and (III-F).

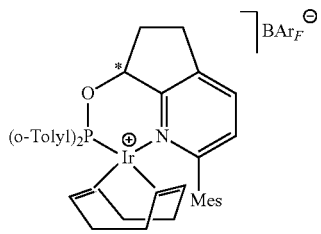
(III-A)

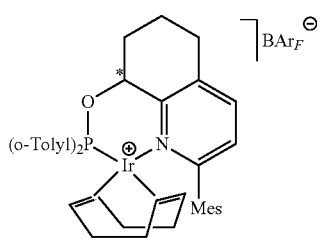
(III-B)

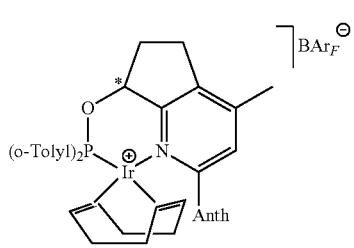
(III-C)

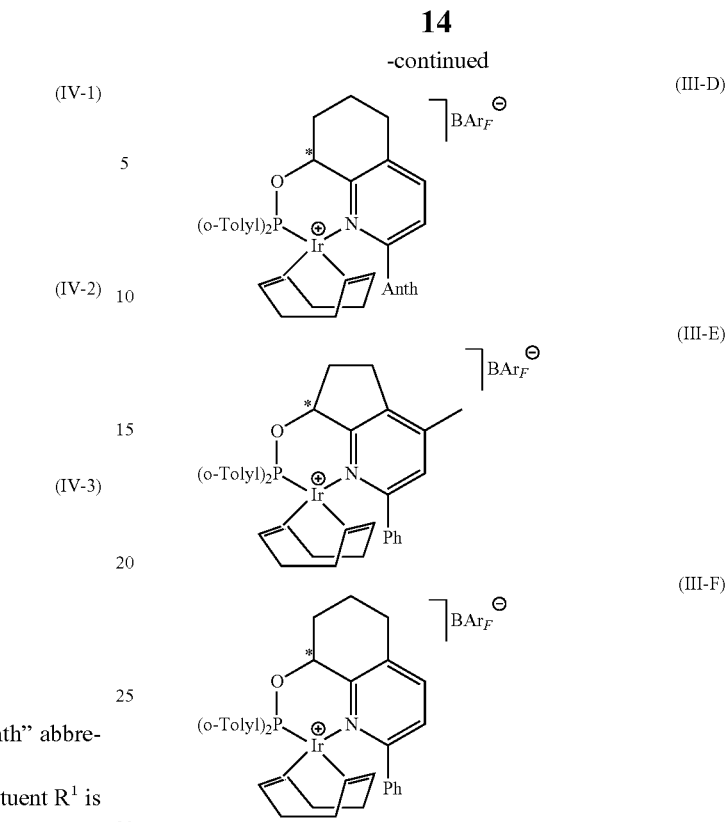

(III-D)

(III-E)

(III-F)

Most preferred as chiral iridium complexes of formula (III) are the complexes of formulae (III-C) and (III-D) and (III-F), particularly the one of formula (III-C) or (III-F).

The chiral iridium complexes of formula (III) can be synthesized accordingly as described in detail in *Chem. Sci.*, 2010, 1, 72-78 whose entire content is hereby incorporated by reference.

The iridium complex of formula (III) is chiral. The chirality at said chiral centre marked by the asterisk is either S or R, i.e. there exist two enantiomers (IIIa) and (IIIb) of the chiral complex of formula (III):

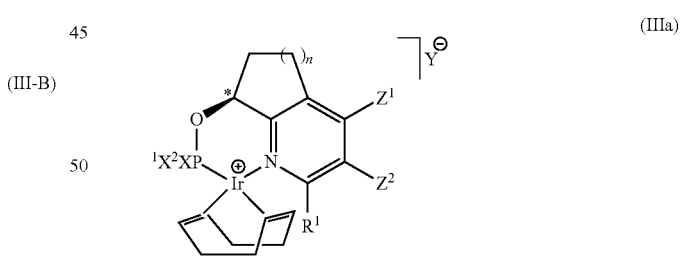
(IIIa)

(S)

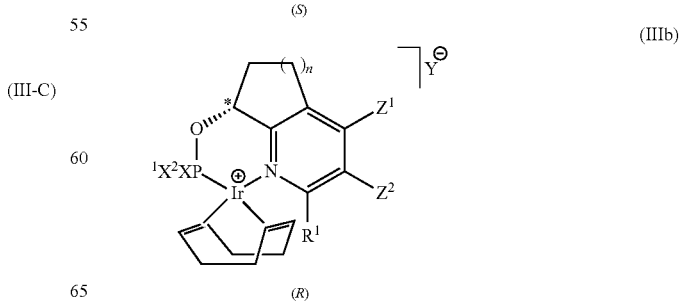
(IIIb)

(R)

The individual enantiomers of the complex of formula (III) could be principally separated after the complexation step from a racemic mixture. However, as *Chem. Sci.*, 2010, 1, 72-78 discloses, the synthesis of the complex of formula (III) comprises a reaction involving a non-racemic chiral alcohol. As it is known that the further reaction steps do not modify the chirality of the complex its isomeric purity (S:R-ratio) is governed therefore by the enantiomeric purity of said alcohol. As said corresponding alcohol can be obtained in a R/S ratio of more than 99% resp. lower than 1%, the complex of formula (III) can be obtained in extremely high enantiomeric purities, particularly in a R/S ratio of more than 99% resp. lower than 1%.

The chiral iridium complex is preferably used in an excess of one enantiomer.

Particularly, it is preferred that the ratio of the molar amounts of the individual enantiomers R:S of the chiral iridium complex of formula (III) is more than 90:10 or less than 10:90, preferably in the range of 100:0 to 98:2 or 0:100 to 2:98. Most preferred is that this ratio is about 100:0 resp. about 0:100. The ultimately preferred ratio is 100:0 resp. 0:100.

In one embodiment the stereogenic centre indicated by * has the R-configuration.

In another embodiment the stereogenic centre indicated by * has the S-configuration.

The hydrogenating agent is molecular hydrogen ($H_2$). The hydrogenation can be carried out in substance or in an inert carrier, particularly in an inert solvent, or a mixture of inert solvents. The hydrogenation is preferred carried out in substance (neat).

Preferred suitable solvents are halogenated hydrocarbons, hydrocarbons, carbonates, ethers and halogenated alcohols.

Particularly preferred solvents are hydrocarbons, fluorinated alcohols and halogenated hydrocarbons, particularly halogenated aliphatic hydrocarbons.

Preferred examples of hydrocarbons are hexane, heptane, toluene, xylene and benzene, particularly toluene and heptane.

Preferred ethers are dialkylethers. Particularly useful ethers are dialklyethers with less than 8 carbon atoms. Most preferred ether is methyl tert.-butyl ether ($CH_3$—O—C($CH_3$)$_3$).

Preferred halogenated alcohols are fluorinated alcohols. A particularly preferred fluorinated alcohol is 2,2,2-trifluoroethanol.

One preferred group of halogenated hydrocarbon are halogenated aromatic compounds, particularly chlorobenzene.

Preferred examples of halogenated aliphatic hydrocarbons are mono- or polyhalogenated linear or branched or cyclic $C_1$- to $C_{15}$-alkanes. Especially preferred examples are mono- or polychlorinated or -brominated linear or branched or cyclic $C_1$- to $C_{15}$-alkanes. More preferred are mono- or polychlorinated linear or branched or cyclic $C_1$- to $C_{15}$-alkanes. Most preferred are dichloromethane, 1,2-dichloroethane, 1,1,1-trichloroethane, chloroform, and methylene bromide.

The most preferred solvent for the hydrogenation is dichloromethane.

The amount of solvent used is not very critical. However, it has been shown that the concentration of the ketal to be hydrogenated is preferably between 0.05 and 1 M, particularly between 0.2 and 0.7 M.

The hydrogenation reaction is conveniently carried out at an absolute pressure of molecular hydrogen from about 1 to about 100 bars, preferably at an absolute pressure of molecular hydrogen from about 20 to about 75 bars. The reaction temperature is conveniently between about 0 to about 100° C., preferably between about 10 to about 60° C.

The sequence of addition of the reactants and solvent is not critical.

The technique and apparatus suitable for the hydrogenation is principally known to the person skilled in the art.

By the asymmetric hydrogenation a prochiral carbon-carbon double bond is hydrogenated to form a chiral stereogenic centre at one or both of the carbon atoms.

As a result of the asymmetric hydrogenation a ketal or acetal having at least one stereogenic carbon centre is formed. Said at least one stereogenic carbon centre is formed from a prochiral carbon-carbon double bond by the asymmetric hydrogenation of the ketal or acetal of the unsaturated ketone.

The ketal or acetal having at least one stereogenic carbon centre has preferably the formula (XI-A) or (XII-A).

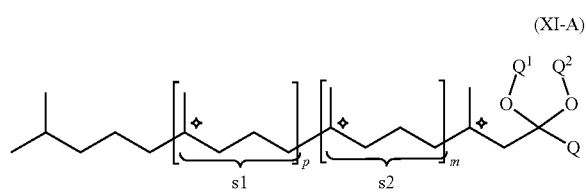

(XI-A)

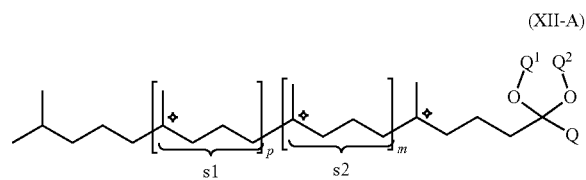

(XII-A)

The groups and symbols in formula (XI-A) and (XII-A) have the same meaning as defined before for formula (XI) and (XII) or (I) and (II).

Next to the ketals or acetals of formula (XI-A) or (XII-A) being mentioned later on in this document the following ketals are particularly 2-methyl-2-((4R,8R)-4,8,12-trimethyltridecyl)-1,3-dioxolane and (R)-2-(4,8-dimethylnonyl)-2-methyl-1,3-dioxolane to be mentioned.

After the asymmetric hydrogenation the asymmetrically hydrogenated ketal or acetal of can be hydrolysed into the corresponding ketone or aldehyde, particularly to formula (I-A) or (II-A)

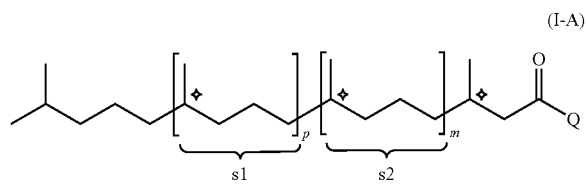

(I-A)

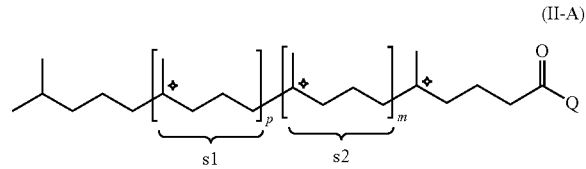

(II-A)

The groups and symbols in formula (I-A) and (II-A) have the same meaning as defined before for formula (I) and (II).

After the asymmetric hydrogenation the asymmetrically hydrogenated ketal or acetal has preferably the formula (XV) or (XVI) or (XVII).

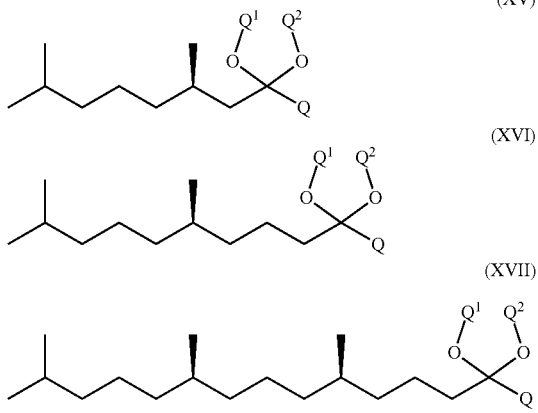

and wherein Q and Q¹ and Q² are as defined for formula (XI) or (XII).

Particularly the ketal or acetal of formula (XV) or (XVI) or (XVII) is selected from the group consisting of formula (XVa), (R)-2-(4,8-dimethylnonyl)-2,5,5-trimethyl-1,3-dioxane, (R)-6,10-dimethyl-2,2-bis(2,2,2-trifluoroethoxy)undecane, and (6R,10R)-6,10,14-trimethyl-2,2-bis(2,2,2-trifluoroethoxy)pentadecane.

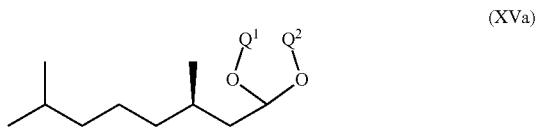

In formula (XVa) Q and Q¹ and Q² are as defined for formula (XI) or (XV).

In one embodiment the ketal or acetal of formula (XI) or (XV) are selected from the group consisting of
(R)-1,1-dimethoxy-3,7-dimethyloctane,
(R)-1,1-dimethoxy-3,7-diethyloctane,
(R)-3,7-dimethyl-1,1-dipropoxyoctane,
(R)-1,1-dibutoxy-3,7-dimethyloctane,
(R)-1,1-diisobutoxy-3,7-dimethyloctane,
(R)-3,7-dimethyl-1,1-bis(2,2,2-trifluoroethoxy)octane,
(R)-2-(2,6-dimethylheptyl)-1,3-dioxolane,
2-((R)-2,6-dimethylheptyl)-4-methyl-1,3-dioxolane,
2-((R)-2,6-dimethylheptyl)-4,5-dimethyl-1,3-dioxolane,
2-((R)-2,6-dimethylheptyl)hexahydrobenzo[d][1,3]dioxole,
(R)-2-(2,6-dimethylheptyl)-1,3-dioxane,
2-((R)-2,6-dimethylheptyl)-5-methyl-1,3-dioxane,
(R)-2-(2,6-dimethylheptyl)-5,5-dimethyl-1,3-dioxane;
(R)-2-(4,8-dimethylnonyl)-2,5,5-trimethyl-1,3-dioxane,
(R)-6,10-dimethyl-2,2-bis(2,2,2-trifluoroethoxy)undecane and (6R,10R)-6,10,14-trimethyl-2,2-bis(2,2,2-trifluoroethoxy)pentadecane.

In a further embodiment the ketal or acetal of formula (XI) or (XV) are selected from the group consisting of (R)-3,7-dimethyl-1,1-bis(2,2,2-trifluoroethoxy)octane, (R)-2-(2,6-dimethylheptyl)-5,5-dimethyl-1,3-dioxane; (R)-2-(4,8-dimethylnonyl)-2,5,5-trimethyl-1,3-dioxane, (R)-6,10-dimethyl-2,2-bis(2,2,2-trifluoroethoxy)undecane and (6R,10R)-6,10,14-trimethyl-2,2-bis(2,2,2-trifluoroethoxy) pentadecane.

As a basic rule the higher the amount of chiral iridium complex in view of the ketal of the unsaturated ketone or the acetal of the unsaturated aldehyde is the higher the yield of the desired product and the better the stereoselectivity is.

From a practical point of view it is preferred not more than 10 mol-%, more preferred not more than 6 mol-%, of the chiral iridium complex in view of the amount of the acetal or ketal to be hydrogenated.

However, in view of the high price of the chiral iridium complex it is desired to use as little amount of iridium complex as possible as long as the yield and the stereoselectivity in the hydrogenated product are acceptable. The threshold of acceptable is at that the desired stereoisomer is least 90% of all the isomers obtained and that the assay yield is at least 50%.

It has been observed that the asymmetric hydrogenation is possible at much lower amount of chiral iridium complex based on the amount of ketal or acetal as compared to the corresponding ketone or aldehyde. The indication of amount of chiral iridium complex may be given in mol-% based on the amount of the acetal or ketal. A different way of indicating the ratio of chiral iridium complex is the molar ratio of ketal or acetal to complex, which in the present document is indicated by S/C ("substrate to complex ratio")

It has been observed that even at amounts as low as 0.02 mol-% (S/C=5,000) in certain cases as low as 0.01 mol-% (S/C=10,000) a high yield of the hydrogenated ketal or acetal is still obtained in high stereoselectivity.

It has been found that the amount can even be substantially lowered when when the hydrogenation is performed in the presence of an additive which is selected from the group consisting of organic sulfonic acids, transition metal salts of organic sulfonic acids, metal alkoxides, aluminoxanes, alkyl aluminoxanes and $B(R)_{(3-v)}(OZ)_v$;

wherein v stands for 0, 1, 2 or 3 and
R stands for F, a $C_{1-6}$-alkyl, a halogenated $C_{1-6}$-alkyl, an aryl or halogenated aryl group; and
Z stands a $C_{1-6}$-alkyl, a halogenated $C_{1-6}$-alkyl, an aryl or halogenated aryl group.

Particularly useful as the transition metal salts of organic sulfonic acids are scandium, indium, yttrium and zirconium salts of organic sulfonic acids.

Metal alkoxides are known to the person skilled in the art. This term particularly relates to the alkoxides of the elements of the group 4 and 13 of the periodic system. It is also known to the person skilled in the art that the metal alkoxides often do not form well-defined structures. Characteristically, metal alkoxides have hydrocarbyl group bound by an oxygen atom to a metal centre. A metal alkoxide may also have different metal centres which are bridged by oxygen or oxygen containing groups, such as for example (polynuclear) aluminium oxoalkoxides.

Particularly useful as metal alkoxides are titanium alkoxides (also being called alkoxy titanates) zirconium alkoxides (also being called alkoxy zirconates) or aluminium alkoxides.

A particularly preferred class of metal alkoxide is of the type of polynuclear aluminium oxoalkoxides such as disclosed in *J. Chem. Soc., Dalton Trans.*, 2002, 259-266 or in *Organometallics* 1993, 12, 2429-2431.

Alkyl aluminoxanes, are known products which are particularly useful as co-catalysts for olefin polymerizations of the Ziegler-Natta type. They are prepared by controlled hydrolysis of trialkylaluminium compound, particularly trimethylaluminium or triethylaluminium. The hydrolysis can be achieved for example by hydrated metal salts (metal salts containing crystal water).

Preferably the additive is selected from the group consisting of triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane and $BF_3$, preferably in the form of a $BF_3$ etherate.

More preferred are triflic acid, alkyl aluminoxanes, particularly methyl aluminoxane, ethyl aluminoxane, tetra alkoxy titanates, $B(R)_{(3-v)}(OZ)_v$; particularly tri-isopropylborate and triethylborane.

Especially good results have been obtained by an additive with has been obtained from trimethylaluminoxane and 2,2,2-trifluoroethanol or from trialkylaluminium and 2,2,2-trifluoroethanol.

One or more of the above mentioned additives can be used for the asymmetric hydrogenation.

It is preferred that the additive is present during the asymmetric hydrogenation in the range of 0.05 to 10 mol-%, particularly in the range of 0.05 to 2 mol-%, as compared to the ketal of the unsaturated ketone or the acetal of the unsaturated aldehyde.

It has been further observed that that the hydrogenation is done further in the presence of a halogenated alcohol, particularly of 2,2,2-trifluoroethanol. a One or more of the halogenated alcohols can be used for the asymmetric hydrogenation.

It has been observed that the amount of chiral iridium complex can be remarkably lowered by addition of the mentioned additive(s), particularly in the combination with the mentioned halogenated alcohol(s), to achieve a given yield and selectivity in the hydrogenation of the mentioned acetals or ketals as compared without the additive(s)/halogenated alcohol(s).

An S/C of more than 30,000, particularly more than 40,000 or more than 50,000 can be achieved. By optimizing the conditions even S/C of more than 100,000 or even 1,000,000 may be achieved.

Hence, the chiral iridium complex can be present during the hydrogenation in an amount in the range from 0.0001 to 5 mol-%, preferably from about 0.001 to about 2 mol-%, more preferably from about 0.001 to about 1 mol-%, most preferably from 0.001 to 0.1 mol-%, based on the amount of the acetal or ketal.

When using a chiral iridium complex the prochiral carbon-carbon double bond is asymmetrically hydrogenated by molecular hydrogen. The complex of a specific absolute configuration yields a specific configuration of the stereogenic carbon centre being formed by the asymmetric hydrogenation.

It has been observed when using a chiral iridium complex of formula (III), that the chiral iridium complexes of formula (III) having the S-configuration at the stereogenic centre indicated by *, yield the R-configuration at the stereogenic centre being formed by the hydrogenation when the prochiral carbon-carbon double bond has the E-configuration, or yield the S-configuration at the stereogenic centre being formed by the hydrogenation when the prochiral carbon-carbon double bond has the Z-configuration.

On the other hand, when the chiral iridium complexes of formula (III) has the R-configuration at the stereogenic centre indicated by *, the hydrogenation of a prochiral carbon-carbon double bond having the Z-configuration yields the R-configuration at the stereogenic centre being formed by the hydrogenation and the hydrogenation of a prochiral carbon-carbon double bond having the E-configuration yields the S-configuration at the stereogenic centre being formed by the hydrogenation.

As particularly, it is preferred to have hydrogenation products having R-configuration at the stereogenic centres being formed it is preferred to use a chiral iridium complex of formula (III) having the S-configuration at the stereogenic centre indicated by * in the case where corresponding prochiral double bond of the acetal or ketal of an unsaturated aldehyde or ketone has the E-configuration; or use a chiral iridium complexes of formula (III) having the R-configuration at the stereogenic centre indicated by * in the case where corresponding prochiral double bond of the acetal or ketal of the unsaturated aldehyde or ketone has the Z-configuration.

In a further aspect the invention relates to a process of manufacturing aldehydes or ketones having at least one stereogenic carbon centre comprising the steps α) forming a ketal from an unsaturated ketone or an acetal of an unsaturated aldehyde and an alcohol or by treating a ketone or an aldehyde with ortho-esters or by trans-ketalization or by trans-acetalization as described already previously in detail in this document;

β) performing a process of asymmetric hydrogenation as described already previously in detail in this document yielding a ketal or acetal having at least one stereogenic carbon centre;

γ) hydrolysing the ketal or acetal having at least one stereogenic carbon centre formed by step β) as described already previously in detail in this document.

The ketones or aldehydes, particularly of formula (I-A) and (II-A) have at at least one stereogenic carbon centre and, hence, are very interesting for the use in the fields of pharma, food supplements and flavours and fragrances or as intermediate products in the synthesis of substances, particularly for the synthesis of tocopherol or vitamin K1.

In a further aspect the invention relates to a composition comprising i) at least one ketal of an unsaturated ketone or at least one acetal of an unsaturated aldehyde;

ii) at least one chiral iridium complex.

The ingredients i) and ii), their preferred embodiments, formulae as well as their formation and preferred ratios i)/ii) are described in detail already above for the process of asymmetric hydrogenation of a ketal of an unsaturated ketone or an acetal of an unsaturated aldehyde by molecular hydrogen in the presence of at least one chiral iridium complex to yield a ketal or acetal having at least one stereogenic carbon centre.

As also already discussed it is very advantageous that said composition further comprises a halogenated alcohol and/or an additive which is selected from the group consisting of organic sulfonic acids, transition metal salts of organic sulfonic acids, metal alkoxides, aluminoxanes, alkyl aluminoxanes and $B(R)_{(3-v)}(OZ)_v$;

wherein v stands for 0, 1, 2 or 3 and

R stands for F, a $C_{1-6}$-alkyl, a halogenated $C_{1-6}$-alkyl, an aryl or halogenated aryl group; and Z stands a $C_{1-6}$-alkyl, a halogenated $C_{1-6}$-alkyl, an aryl or halogenated aryl group.

As was shown above such a new composition enables a very efficient asymmetric hydrogenation by molecular hydrogen. As this composition allows the efficient manufacturing of asymmetrically hydrogenated acetals or ketals, respectively their corresponding aldehydes or ketones, which can be used as intermediates for the synthesis of chiral compounds the above mentioned composition is important for the use for the synthesis of chiral compounds.

Particularly of relevance is the ketal of formula (XX-A)

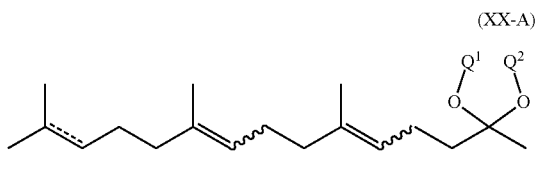

wherein $Q^1$ and $Q^2$ are as defined in detail before for formula (XI) and (XII) and wherein the double bond having dotted lines ( ----- ) represent either a single carbon-carbon bond or a double carbon-carbon bond.

Particularly of relevance is the ketal of formula (XX-B)

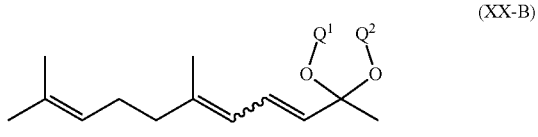

wherein $Q^1$ and $Q^2$ are as defined in detail before for formula (XI) and (XII) and where a wavy line represents a carbon-carbon bond which is linked to the adjacent carbon-carbon double bond so as to have said carbon-carbon double bond either in the Z or in the E-configuration.

Particularly of relevance is the acetal of formula (XX-C)

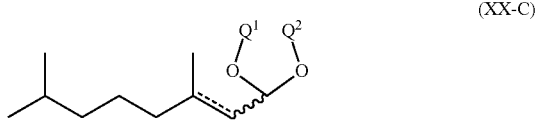

wherein $Q^1$ and $Q^2$ are as defined in detail before for formula (XI) and (XII) and wherein the double bond having dotted lines ( ----- ) represent either a single carbon-carbon bond or a double carbon-carbon bond; and wherein a wavy line represents a carbon-carbon bond which is linked to an adjacent single carbon bond ( ----- ) representing ( — ) or to an adjacent carbon-carbon double bond ( ===== ) representing ( = ) so as to have said carbon-carbon double bond either in the Z or in the E-configuration.

Particularly of relevance is the is the acetal of formula (XXI-A) or (XXI-B) or (XXI-C) or (XXI-D)

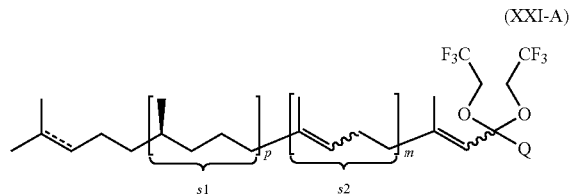

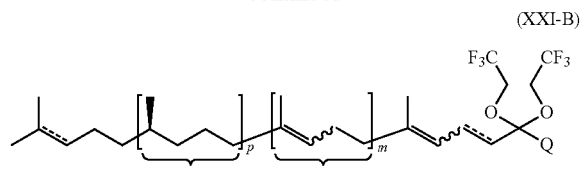

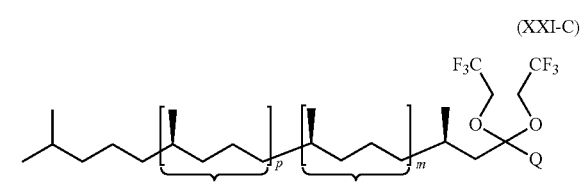

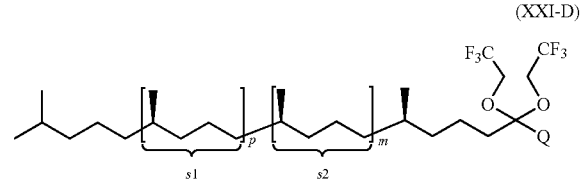

wherein Q stands for H or $CH_3$ and m and p stand independently from each other for a value of 0 to 3 with the proviso that the sum of m and p is 0 to 3, wherein the double bond having dotted lines ( ----- ) in the above formulae represents either a single carbon-carbon bond or a double carbon-carbon bond; and wherein a wavy line represents a carbon-carbon bond which is linked to an adjacent single carbon bond ( ----- ) representing ( — ) or to an adjacent carbon-carbon double bond ( ===== ) representing ( = ) so as to have said carbon-carbon double bond either in the Z or in the E-configuration.

All these compounds of formula (XX-A), (XX-B), (XX-C), (XXI-A), (XXI-B), (XXI-C) or (XXI-D) are sub groups of the acetals or ketals of compound of formula (I) or (II) or acetals or ketones of the compound of formula (I-A) or (I-B) have shown to be very interesting as starting material or product of the process of manufacturing compound of formula (I-A) or (I-B) or an acetal or a ketal thereof described in detail before.

Particularly of relevance is the acetal of formula (XXI-A) or (XXI-B) or (XXI-C) or (XXI-D)

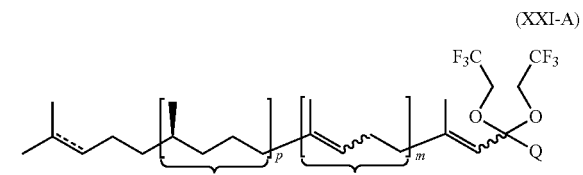

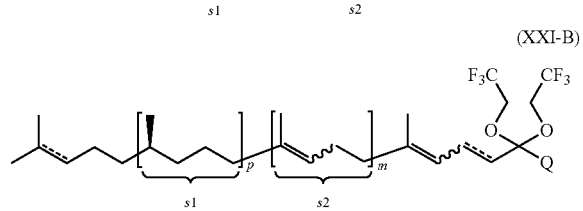

-continued

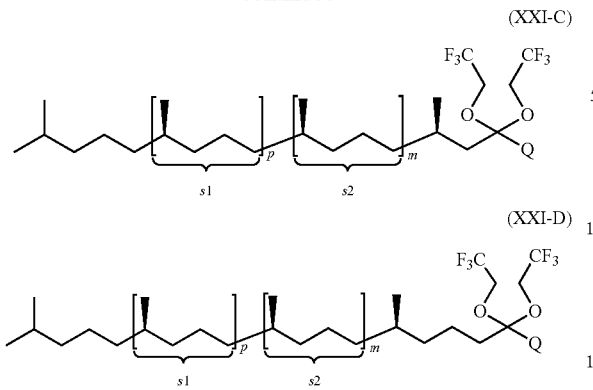

(XXI-C)

(XXI-D)

wherein Q stands for H or CH₃ and m and p stand independently from each other for a value of 0 to 3 with the proviso that the sum of m and p is 0 to 3, wherein the double bond having dotted lines ( ===== ) in the above formulae represents either a single carbon-carbon bond or a double carbon-carbon bond; and wherein a wavy line represents a carbon-carbon bond which is linked to an adjacent single carbon bond ( ===== ) representing ( — ) or to an adjacent carbon-carbon double bond ( ===== ) representing ( = ) so as to have said carbon-carbon double bond either in the E-configuration.

All these compounds of formula (XX-A), (XX-B), (XX-C), (XXI-A), (XXI-B), (XXI-C) or (XXI-D) are sub groups of the acetals or ketals of compound of formula (I) or (II) or acetals or ketones of the compound of formula (I-A) or (I-B) have shown to be very interesting as starting material or product of the process of manufacturing compound of formula (I-A) or (I-B) or an acetal or a ketal thereof described in detail before.

Hence, in a still further aspect the invention relates to the use of the above composition for the synthesis of chiral compounds, particularly of (6R,10R)-6,10,14-trimethylpentadecan-2-one, (3RS,7R,11R)-3,7,11,15-tetramethylhexadec-1-en-3-ol), (2-ambo)-α-tocopherol or (2R,4'R,8'R)-α-tocopherol.

EXAMPLES

The present invention is further illustrated by the following experiments.

GC Determination of E/Z-ratio and/or purity of 6,10-dimethylundec-5-en-2-one (DHGA), (R)-6,10-dimethylundecan-2-one (THGA) and (R)-6, 10, 14-trimethylpentadec-5-en-2-one (R-THFA)

Agilent 6850, column DB-5HT (30 m, 0.25 mm diameter, 0.10 μm film thickness), 107 kPa helium carrier gas). The samples were injected as solutions in hexane, split ratio 300:1, injector temperature 200° C., detector temperature 350° C. Oven temperature program: 100° C. (8 min), 10° C./min to 200° C. (1 min), 20° C./min to 220° C. (4 min), runtime 24 min.

GC Determination of purity of (6R,10R)-6, 10, 14-trimethylpentadecan-2-one

Agilent 6850, column DB-5HT (30 m, 0.25 mm diameter, 0.10 μm film thickness), 115 kPa helium carrier gas). The samples were injected as solutions in hexane, split ratio 300:1, injector temperature 200° C., detector temperature 350° C. Oven temperature program: 120° C. (5 min), 14° C./min to 260° C. (2 min), 20° C./min to 280° C. (4 min), runtime 22 min.

GC Determination of purity of (3RS,7R,11R)-3, 7, 11, 15-tetramethylhexadec-1-en-3-ol ((R,R)-Isophytol)

Agilent 6850 instrument equipped with FID. Agilent DB-5 column (30 m, 0.32 mm diameter, 0.25 μm film thickness) with 25 psi molecular hydrogen carrier gas. The samples were injected as solutions in acetonitrile with a split ratio of 50:1. Injector temperature: 250° C., detector temperature: 350° C. Oven temperature program: 100° C., 4° C./min to 250° C.

GC Determination of E/Z-ratio and/or purity of 6,10,14-trimethylpentadeca-5,9-dien-2-one, 6, 10, 14-trimethylpentadeca-5, 9, 13-trien-2-one, 6,10-dimethylundeca-5,9-dien-2-one and ketals Agilent 6850 instrument, column Agilent DB-5 (123-5032E, 30 m×0.32 mm, film 0.25 μm), the samples were injected as solutions in acetonitrile, split ratio 50:1, injector 250° C., detector 350° C. Oven temperature program: 100° C., 4° C./min until 250° C., 37.5 min total runtime.

| Retention times ($t_R$): | min. |
|---|---|
| E-Citral-DM | 8.6 |
| Z-Citral-DM | 8.0 |
| E-Citral-neo | 15.2 |
| Z-Citral-neo | 14.0, pc[1] |
| (5E,9E)-6,10,14-trimethylpentadeca-5,9,13-trien-2-one (EE-FA) | 22.2 |
| EE-FA-DM | decomp.[2] |
| EE-FA-tfe | 23.1, pc[1] |
| (5Z,9Z)-6,10,14-trimethylpentadeca-5,9,13-trien-2-one (ZZ-FA) | 21.0 |
| ZZ-FA-DM | 23.0, pc[1] |
| ZZ-FA-neo | 27.9 |
| (5E,9E)-6,10,14-trimethylpentadeca-5,9-dien-2-one (EE-DHFA) | 21.2 |
| EE-DHFA-DM | 24.6, pc[1] |
| EE-DHFA-neo | 29.5 |
| EE-DHFA-tfe | 22.4 |
| (5Z,9Z)-6,10,14-trimethylpentadeca-5,9-dien-2-one (ZZ-DHFA) | 20.0 |
| ZZ-DHFA-DM | 23.0, pc[1] |
| ZZ-DHFA-neo | 27.9 |
| (E)-6,10-dimethylundeca-5,9-dien-2-one (E-GA) | 11.0 |
| E-GA-DM | 14.8 |
| E-GA-neo | 20.5 |
| E-GA-tfe | 13.2, pc[1] |
| (Z)-6,10-dimethylundeca-5,9-dien-2-one (Z-GA) | 10.6 |
| Z-GA-DM | 14.0, pc[1] |
| Z-GA-neo | 19.5 |
| E-DHGA-DM | 14.1, pc[1] |
| E-DHGA-neo | 19.6, pc[1] |
| E-DHGA-tfe | 12.5 |
| Z-DHGA-DM | 13.0, pc[1] |
| Z-DHGA-neo | 18.5, pc[1] |
| R-Tetrahydrocitral-neo | 12.6 |
| R,E-THFA-DM | 24.2, pc[1] |
| R,E-THFA-neo | 29.1 |
| R,Z-THFA-DM | 23.1, pc[1] |
| R,Z-THFA-neo | 27.9 |
| R-THGA-DM | 13.1 |
| R-THGA-neo | 18.9 |
| R-THGA-tfe | 11.8 |
| RR-C18-DM | decomp.[2] |

-continued

| Retention times ($t_R$): | min. |
|---|---|
| RR-C18-neo | 28.5 |
| RR-C18-tfe | 21.4 |

[1] pc= partial decomposition
[2] decomp.= decomposition during GC analysis

Analysis of the Asymmetrically Hydrogenated Reaction Products

The corresponding dimethyl, ethylene glycol, neopentyl and bis(trifluoroethyl) ketals were hydrolyzed to the ketones in the presence of aqueous acid and analyzed for conversion and their stereoisomer ratio using the following methods for ketones.

The conversion of the hydrogenation reaction was determined by gas chromatography using an achiral column.

Method for Conversion:

Agilent 7890A GC equipped with FID. Agilent HP-5 column (30 m, 0.32 mm diameter, 0.25 μm film thickness) with 25 psi molecular hydrogen carrier gas. The samples were injected as solutions in dichloromethane with a split ratio of 10:1. Injector temperature: 250° C., detector temperature: 300° C. Oven temperature program: 50° C. (2 min) then 15° C./min to 300° C., hold 5 min.

For the determination of the isomer ratio, the hydrogenated ketones can be reacted with either (+)-diisopropyl-O,O'-bis(trimethylsilyl)-L-tartrate or (−)-diisopropyl-O,O'-bis(trimethylsilyl)-D-tartrate in the presence of trimethylsilyl triflate [Si(CH$_3$)$_3$(OSO$_2$CF$_3$)] to form the diastereomeric ketals as described in A. Knierzinger, W. Walther, B. Weber, R. K. Müller, T. Netscher, *Helv. Chim. Acta* 1990, 73, 1087-1107. The ketals can be analysed by gas chromatography using an achiral column to determine the isomer ratios. For the hydrogenated ketone 6,10-dimethylundecan-2-one, either D-(−)- or L-(+)-diisopropyltartrate can be used. For 6,10,14-trimethylpentadecan-2-one, L-(+)-diisopropyltartrate can be used to measure the quantity of the (6R,10R)-isomer that was present. D-(−)-diisopropyltartrate can be used to determine the amount of the (6S,10S)-isomer. Thus the selectivity of the stereoselective hydrogenation can be determined indirectly.

Method for Determination of Isomers:

Agilent 6890N GC with FID. Agilent CP-Si188 for FAME column (60 m, 0.25 mm diameter, 0.20 μm film thickness) with 16 psi molecular hydrogen carrier gas. The samples were injected as solutions in ethyl acetate with a split ratio of 5:1. Injector temperature: 250° C., FID detector temperature: 250° C. Oven temperature program: 165° C. (isothermal, 240 min)

The Ir complexes indicated in the following experiments are prepared according to the disclosure in *Chem. Sci.*, 2010, 1, 72-78.

Preparation of Additives

MAO/TFE: A 1.6 M MAO (MAO: methylaluminoxane solution in toluene (0.64 mL) was quenched with 2,2,2-trifluoroethanol (TFE) (3.1 mmol), leading to small excess of free TFE.

EAO/TFE: A 10 wt % EAO (EAO: ethylaluminoxane solution in toluene (1 mmol) was quenched with TFE (3.2 mmol), leading to small excess of free TFE.

TMA/TFE: A 2 M TMA (TMA: trimethylaluminum (Al(CH$_3$)$_3$)) solution in heptane (1 mmol) was quenched with TFE (3.1 mmol), leading to small excess of free TFE.

TEA/TFE: A 2 M TEA (TEA: triethylaluminum (Al(CH$_2$CH$_3$)$_3$)) solution in heptane (1 mmol) was quenched with TFE (3.1 mmol), leading to small excess of free TFE.

TMA/BHT/TFE: A 2 M TMA solution in heptane (1 mmol) was quenched with 2,6-di-tert-butyl-4-methylphenol (BHT) (2 mmol) and subsequently with TFE (3.1 mmol), leading to small excess of free TFE.

Ti(OCH$_2$CF$_3$)$_4$: Tetraisopropyl orthotitanate (8.1 mmol) was dissolved in 2,2,2-trifluoroethanol at 50° C. Removal of the solvent gave Ti(OCH$_2$CF$_3$)$_4$ as a white residue which was isolated and identified to be Ti(OCH$_2$CF$_3$)$_4$.

These additives were freshly prepared and used either as a heterogeneous mixture at room temperature or homogeneous by heating to a temperature between 50° and 70° C.

The additives tetraisopropyl orthotitanate (Ti(OiPr)$_4$), triisopropylborate (B(OiPr)$_3$), yttrium triflate (Y(OTf)$_3$), scandium triflate (Sc(OTf)$_3$), sodium tetrakis[3,5-bis(trifluoromethyl)phenyl]borate (NaBAr$_F$) and triethyl borane (TEB) (1 M solution in hexane) are commercially available as were used as received.

Experiment E1

Preparation of Ketals of Unsaturated Ketones a) Preparation of Dimethyl Ketals

The corresponding ketone of tables 1a-1c (170.5 mmol) was added to trimethyl orthoformate (50.8 mL, 49.2 g, 451 mmol, 2.65 eq.) and cooled to 5° C. Sulfuric acid (96%, 32.3 mg, 0.29 mmol, 0.2 mol %) in MeOH (16 mL) was added within 5 min. Subsequently, the reaction was heated to reflux (65° C. IT) for 3 h. After cooling, thin layer chromatography (TLC) analysis indicated full conversion. NaOMe (0.24 mL of a 25% solution in MeOH) was added to neutralize the acid. The mixture was concentrated in vacuo and subsequently diluted with hexane (50 mL). The developed precipitate was filtered off and the filtrate was concentrated. The crude product was purified by distillation, furnishing the desired dimethyl ketal the characterization of which is given in detail hereafter.

TABLE 1a

Preparation of dimethyl ketals of 6,10-dimethylundeca-5,9-dien-2-one and 6,10-dimethylundec-5-en-2-one.

| | E-GA-DM | Z-GA-DM | E-DHGA-DM | Z-DHGA-DM |
|---|---|---|---|---|
| Ketone | (E)-6,10-dimethyl-undeca-5,9-dien-2-one | (Z)-6,10-dimethyl-undeca-5,9-dien-2-one | (E)-6,10-dimethyl-undec-5-en-2-one | (Z)-6,10-dimethyl-undec-5-en-2-one |
| Ketal | (E)-10,10-dimethoxy-2,6-dimethylundeca-2,6-diene | (Z)-10,10-dimethoxy-2,6-dimethylundeca-2,6-diene | (E)-2,2-dimethoxy-6,10-dimethylundec-5-ene | (Z)-2,2-dimethoxy-6,10-dimethylundec-5-ene |
| Yield[%] | 87 | 73 | 91 | 98 |
| E/Z | 99.4/0.6 | 1.6/98.4 | 95.4/4.6 | 0.4/99.6 |

TABLE 1b

Preparation of dimethyl ketals of 6,10,14-trimethylpentadeca-5,9,13-trien-2-one and 6,10,14-trimethylpentadeca-5,9-dien-2-one.

| | EE-FA-DM | EE-DHFA-DM | ZZ-DHFA-DM |
|---|---|---|---|
| Ketone | (5E,9E)-6,10,14-trimethyl-pentadeca-5,9,13-trien-2-one | (5E,9E)-6,10,14-trimethyl-pentadeca-5,9-dien-2-one | (5Z,9Z)-6,10,14-trimethyl-pentadeca-5,9-dien-2-one |
| Ketal | (6E,10E)-14,14-dimethoxy-2,6,10-trimethyl-pentadeca-2,6,10-triene | (5E,9E)-2,2-dimethoxy-6,10,14-trimethyl-pentadeca-5,9-diene | (5Z,9Z)-2,2-dimethoxy-6,10,14-trimethyl-pentadeca-5,9-diene |
| Yield[%] | 95 | 90 | 56 |
| Purity[1] | 95.1 | 99.0 | 96.5 |

[1]Purity determined by quantitative $^1$H-NMR.

TABLE 1c

Preparation of dimethyl ketals of (R)-6,10,14-trimethylpentadec-5-en-2-one.

| | R,E-THFA-DM | R,Z-THFA-DM |
|---|---|---|
| Ketone | (R,E)-6,10,14-trimethylpentadec-5-en-2-one | (R,Z)-6,10,14-trimethylpentadec-5-en-2-one |
| Ketal | (R,E)-2,2-dimethoxy-6,10,14-trimethylpentadec-5-ene | (R,Z)-2,2-dimethoxy-6,10,14-trimethylpentadec-5-ene |
| Yield[%] | 92 | 87 |
| Purity[1] | 94.8 | 98.2 |

[1]Purity determined by quantitative $^1$H-NMR.

Characterization Data (E)-10,10-dimethoxy-2,6-dimethylundeca-2,6-diene
(E-GA-DM)

$^1$H NMR (300 MHz, CDCl$_3$): δ 1.26 (s, 3H), 1.58 (s, 3H), 1.60 (s, 3H), superimposed by 1.60-1.65 (m, 2H), 1.66 (br s, 3H), 1.92-2.09 (m, 6H), 3.17 (s, 6H), 5.02-5.14 (m, 2H) ppm.

$^{13}$C NMR (75 MHz, CDCl$_3$): δ 15.9 (1C), 17.6 (1C), 20.8 (1C), 22.8 (1C), 25.6 (1C), 26.6 (1C), 36.4 (1C), 39.6 (1C), 47.9 (2C), 101.4 (1C), 123.8 (1C), 124.2 (1C), 131.2 (1C), 135.1 (1C) ppm.

MS (EI, m/z): 240 (M+, <1), 225.3 [(M-CH$_3$)$^+$, 1], 209.3 [(M-CH$_3$O)$^+$, 20], 193.3 (8), 176.2 (18), 161.2 (16), 139.2 (20), 123.2 (14), 107.2 (75), 89.2 (100), 69.2 (65), 41.1 (56).

IR (cm$^{-1}$): 2928 (m), 2857 (w), 2828 (w), 1670 (w), 1452 (m), 1376 (s), 1345 (w), 1302 (w), 1262 (w), 1222 (w), 1196 (m), 1172 (m), 1123 (s), 1102 (s), 1053 (m), 985 (w), 929 (w), 854 (s), 744 (w), 619 (w).

(Z)-10,10-dimethoxy-2,6-dimethylundeca-2,6-diene
(Z-GA-DM)

$^1$H NMR (300 MHz, CDCl3): δ 1.27 (s, 3H), 1.56-1.65 (m, 5H), 1.68 (br. s, 6H), 1.96-2.09 (m, 6H), 3.17 (s, 6H), 5.11 (t, J=7.2 Hz, 2H) ppm.

$^{13}$C NMR (75 MHz, CDCl$_3$): δ 17.6 (1C), 20.9 (1C), 22.7 (1C), 23.3 (1C), 25.7 (1C), 26.6 (1C), 31.9 (1C), 36.7 (1C), 48.0 (2C), 101.4 (1C), 124.2 (1C), 124.6 (1C), 131.5 (1C), 135.4 (1C) ppm.

MS (EI, m/z): No GC-MS was obtained due to decomposition on the column.

IR (cm$^{-1}$): 2943 (m), 2858 (w), 2828 (w), 1451 (m), 1376 (m), 1348 (w), 1301 (w), 1261 (w), 1197 (m), 1172 (m), 1153 (w), 1120 (s), 1098 (m), 1053 (s), 929 (w), 854 (m), 833 (m), 745 (w), 622 (w).

(E)-2,2-dimethoxy-6,10-dimethylundec-5-ene
(E-DHGA-DM)

$^1$H NMR (300 MHz, CDCl$_3$): δ 0.83 (d, J=6.6 Hz, 6H), 1.02-1.13 (m, 2H), 1.24 (s, 3H), 1.27-1.39 (m, 2H), 1.49 (tqq, J=6.4, 6.4, 6.4 Hz, 1H), superimposed by 1.53-1.63 (m, 2H), superimposed by 1.56 (s, 3H), 1.87-2.03 (m, 4H), 3.13 (s, 6H), 5.07 (tq, J=7.0, 1.4 Hz, 1H) ppm.

$^{13}$C NMR (75 MHz, CDCl$_3$): δ 16.1 (1C), 21.2 (1C), 23.0 (2C), 23.2 (1C), 26.0 (1C), 28.2 (1C), 36.9 (1C), 39.0 (1C), 40.2 (1C), 48.3 (2C), 101.8 (1C), 124.0 (1C), 135.9 (1C) ppm.

MS (EI, m/z): No GC-MS was obtained due to decomposition on the column.

IR (cm$^{-1}$): 2953 (s), 2931 (s), 2870 (m), 2828 (m), 2108 (w), 1668 (w), 1460 (m), 1377 (s), 1367 (m), 1345 (w), 1301 (w), 1262 (m), 1221 (m), 1198 (m), 1172 (s), 1119 (s), 1100 (s), 1077 (s), 1053 (s), 967 (w), 927 (w), 854 (w), 796 (w), 739 (w), 620 (w).

(Z)-2,2-dimethoxy-6,10-dimethylundec-5-ene
(Z-DHGA-DM)

$^1$H NMR (300 MHz, CDCl$_3$): δ 0.88 (d, J=6.6 Hz, 6H), 1.12-1.21 (m, 2H), 1.28 (s, 3H), 1.32-1.43 (m, 2H), 1.53 (dspt, J=6.6, 6.6 Hz, 1H), 1.57-1.66 (m, 2H), 1.68 (q, J=1.1 Hz, 3H), 1.94-2.06 (m, 4H), 3.18 (s, 6H), 5.10 (t, J=6.8 Hz, 1H) ppm.

$^{13}$C NMR (75 MHz, CDCl$_3$): δ 20.9 (1C), 22.6 (2C), 22.7 (1C), 23.3 (1C), 25.8 (1C), 27.9 (1C), 31.9 (1C), 36.8 (1C), 38.9 (1C), 48.0 (2C), 101.5 (1C), 124.3 (1C), 135.9 (1C) ppm.

MS (EI, m/z): No GC-MS was obtained due to decomposition on the column.

IR (cm$^{-1}$): 2953 (s), 2870 (w), 2828 (w), 1461 (w), 1376 (m), 1301 (w), 1261 (m), 1205 (m), 1172 (m), 1119 (m), 1097 (m), 1074 (m), 1053 (s), 1022 (w), 927 (m), 854 (m), 738 (w), 621 (w).

(5E,9E)-6,10,14-trimethyl-pentadeca-5,9,13-trien-2-one (EE-FA-DM)

$^1$H-NMR (300.1 MHz, CDCl$_3$): δ=1.28 (s, 2-CH$_3$), 1.56-1.70 (m, 4 CH$_3$+CH$_2$), 1.92-2.12 (m, 10H), 3.18 (s, 2 OCH$_3$), 5.05-5.17 (m, 3H$_{olefin}$).

$^{13}$C-NMR (75.5 MHz, CDCl$_3$): δ=16.0 (2C), 17.7, 20.9, 22.8, 25.7, 26.6, 26.8, 36.5, 39.67, 39.72, 48.0 (2 OCH$_3$), 101.5 (C-2), 123.8 and 124.2 and 124.4 (3C$_{olefin}$), 131.3 and 135.0 and 135.3 (3 C$_{olefin}$).

IR (ATR, cm$^{-1}$): 2924s, 2856w, 2828w, 1668m, 1450s, 1376s, 1346w, 1302m, 1261m, 1222m, 1196m, 1172m, 1153w, 1123s, 1053s, 985w, 929w, 854s, 744m, 620w

MS (m/z): 308 (M+, 0.1%), 293 [(M-15)$^+$, 0.2], 276 [(M-CH$_3$OH)$^+$, 6], 244 [(M-2CH$_3$OH)$^+$, 4], 207 [(M-CH$_3$OH—C$_5$H$_9$)$^+$, 11], 175 [(M-2CH$_3$OH—C$_5$H$_9$)$^+$, 19], 107 [(M-2CH$_3$OH-2C$_5$H$_9$+H)$^+$, 71], 69 (C$_5$H$_9$$^+$, 100).

(5E,9E)-6,10,14-trimethylpentadeca-5,9-dien-2-one
(EE-DHFA-DM)

$^1$H NMR (300 MHz, CDCl$_3$): δ 0.87 (d, J=6.6 Hz, 6H), 1.06-1.17 (m, 2H), 1.28 (s, 3H), 1.31-1.42 (m, 2H), 1.53

(tqq, J=6.6, 6.6, 6.6 Hz, 1H), superimposed by 1.58 (s, 3H), superimposed by 1.58-1.65 (m, 2H), superimposed by 1.62 (s, 3H), 1.90-2.11 (m, 8H), 3.18 (s, 6H), 5.06-5.15 (m, 2H) ppm.

$^{13}$C NMR (75 MHz, CDCl$_3$): δ 16.3 (1C), 16.4 (1C), 21.3 (1C), 23.0 (2C), 23.3 (1C), 26.2 (1C), 27.0 (1C), 28.3 (1C), 36.9 (1C), 39.0 (1C), 40.1 (1C), 40.3 (1C), 48.4 (2C), 101.9 (1C), 124.25 (1C), 124.31 (1C), 135.66 (1C), 135.71 (1C) ppm.

MS (EI, m/z): No GC-MS was obtained due to decomposition on the column.

IR (cm$^{-1}$): 2953 (m), 2930 (m), 2870 (m), 2828 (w), 1668 (w), 1457 (m), 1377 (m), 1345 (w), 1302 (w), 1262 (m), 1222 (m), 1196 (m), 1172 (m) 1123 (s), 1054 (s), 929 (w), 854 (s), 739 (w), 620 (w).

(5Z,9Z)-6,10,14-trimethylpentadeca-5,9-dien-2-one (ZZ-DHFA-DM)

$^1$H NMR (300 MHz, CDCl$_3$): δ 0.88 (d, J=6.6 Hz, 6H), 1.11-1.21 (m, 2H), 1.28 (s, 3H), 1.30-1.43 (m, 2H), 1.54 (qq, J=6.6 Hz, 1H), superimposed by 1.57-1.66 (m, 2H), 1.67 (br s, 3H), 1.69 (q, J=1.3 Hz, 3H), 1.94-2.10 (m, 8H), 3.18 (s, 6H), 5.12 (t, J=6.4 Hz, 2H) ppm.

$^{13}$C NMR (75 MHz, CDCl$_3$): δ 20.9 (1C), 22.3 (1C), 22.6 (1C), 22.7 (1C), 23.39 (1C), 23.40 (1C), 25.8 (1C), 26.3 (1C), 27.9 (1C), 31.9 (1C), 32.2 (1C), 36.7 (1C), 38.9 (1C), 48.0 (2C), 101.4 (1C), 124.6 (1C), 124.7 (1C), 135.4 (1C), 135.8 (1C) ppm.

MS (EI, m/z): No GC-MS was obtained due to decomposition on the column.

IR (cm$^{-1}$): 2953 (m), 2870 (m), 2828 (w), 1454 (m), 137 (m), 1302 (w), 1261 (m), 1201 (m), 1172 (m), 1152 (m), 1098 (m), 1054 (s), 854 (s), 749 (w), 622 (w).

(R,E)-2,2-dimethoxy-6,10,14-trimethylpentadec-5-ene (R,E-THFA-DM)

$^1$H NMR (300 MHz, CDCl$_3$): δ 0.84 (d, J=6.6 Hz, 3H), superimposed by 0.86 (d, J=6.6 Hz, 6H), 0.99-1.44 (m, 11H), superimposed by 1.28 (s. 3H), 1.52 (tqq, J=6.6, 6.6, 6.6 Hz, 1H), 1.60 (s, 3H), 1.60-1.66 (m, 2H), 1.90-2.05 (m, 4H), 3.18 (s, 6H), 5.10 (tq, J=7.1, 1.1 Hz, 1H) ppm.

$^{13}$C NMR (75 MHz, CDCl$_3$): δ 16.3 (1C), 20.1 (1C), 21.3 (1C), 23.0 (1C), 23.1 (1C), 23.2 (1C), 25.2 (1C), 25.7 (1C), 28.4 (1C), 33.1 (1C), 36.9 (1C), 37.1 (1C), 37.7 (1C), 39.8 (1C), 40.3 (1C), 48.4 (2C), 101.9 (1C), 124.0 (1C), 136.0 (1C) ppm.

MS (EI, m/z): No GC-MS was obtained due to decomposition on the column.

IR (cm$^{-1}$): 2952 (m), 2927 (s), 2869 (m), 2828 (w), 1461 (m), 1377 (m), 1301 (w), 1262 (m), 1222 (m), 1197 (m), 1172 (m), 1120 (m), 1101 (m), 1076 (m), 1054 (m), 930 (w), 854 (m), 737 (w), 620 (w).

(R,Z)-2,2-dimethoxy-6,10,14-trimethylpentadec-5-ene (R,Z-THFA-DM)

$^1$H NMR (300 MHz, CDCl$_3$): δ 0.85 (d, J=6.4 Hz, 3H), superimposed by 0.87 (d, J=6.4 Hz, 6H), 1.01-1.27 (m, 7H), 1.28 (s, 3H), 1.29-1.44 (m, 4H), 1.53 (dqq, J=6.5, 6.5 Hz, 1H), 1.58-1.66 (m, 2H), 1.68 (q, J=1.1 Hz, 3H), 1.91-2.08 (m, 4H), 3.18 (s, 6H), 5.11 (t, J=6.8 Hz, 1H) ppm.

$^{13}$C NMR (75 MHz, CDCl$_3$): δ) 19.7 (1C), 20.9 (1C), 22.60 (1C), 22.69 (1C), 22.71 (1C), 23.4 (1C), 24.8 (1C), 25.5 (1C), 28.0 (1C), 32.0 (1C), 32.7 (1C), 36.8 (1C), 37.0 (1C), 37.3 (1C), 39.3 (1C), 48.0 (2C), 101.5 (1C), 124.3 (1C), 135.9 (1C) ppm.

MS (EI, m/z): No GC-MS was obtained due to decomposition on the column.

IR (cm$^{-1}$): 2952 (m), 2927 (m), 2869 (m), 2828 (w), 1462 (m), 1376 (m), 1301 (w), 1261 (w), 1197 (w), 1172 (m), 1119 (m), 1098 (m), 1074 (m), 1054 (s), 1022 (w), 854 (m), 736 (w), 622 (w).

b) Preparation of Ethylene Glycol Ketals

Under nitrogen, a reaction vessel was charged with glycol (112 mL, 125 g, 2.1 mol), p-toluenesulfonic acid monohydrate (0.150 g, 0.5774 mmol) and 0.5 mol of the ketone as indicated in table 1d or 1e. The mixture was allowed to stir at ambient temperature for 5 hours at reduced pressure (0.39 mbar). While maintaining the low pressure, the temperature was slowly increased to 40° C. At conversion of larger than 95% of the ketone, the temperature was further increased allowing a gentle distillation of glycol and continued until a conversion of more than 99% was achieved.

At room temperature, the product was extracted by a solution of triethylamine in heptane (2 mL triethylamine/L heptane). The glycol phase was separated and the heptane layer was washed with a NaHCO$_3$ solution in water. Separation of the heptane phase, drying over anhydrous Na$_2$SO$_4$, filtration and removal of the solvent in vacuo gave the crude ketal. The ketal was further purified by means of distillation. The corresponding ketal was identified by $^1$H-NMR.

TABLE 1d

Preparation of ethylene glycol ketals of 6,10-dimethylundec-5-en-2-one.

|  | E-DHGA-en | Z-DHGA-en |
| --- | --- | --- |
| Ketone | (E)-6,10-dimethylundec-5-en-2-one | (Z)-6,10-dimethylundec-5-en-2-one |
| Ketal | (E)-2-(4,8-dimethylnon-3-en-1-yl)-2-methyl-1,3-dioxolane | (Z)-2-(4,8-dimethylnon-3-en-1-yl)-2-methyl-1,3-dioxolane |
| Yield [%] | 88 | 87 |

TABLE 1e

Preparation of ethylene glycol ketals of 6,10,14-trimethylpentadeca-5,9,13-trien-2-one and 6,10,14-trimethylpentadeca-5,9-dien-2-one.

|  | EE-FA-en | EE-DHFA-en | ZZ-DHFA-en |
| --- | --- | --- | --- |
| Ketone | (5E,9E)-6,10,14-trimethyl-pentadeca-5,9,13-trien-2-one | (5E,9E)-6,10,14-trimethyl-pentadeca-5,9-dien-2-one | (5Z,9Z)-6,10,14-trimethyl-pentadeca-5,9-dien-2-one |
| Ketal | 2-methyl-2-((3E,7E)-4,8,12-trimethyl-trideca-3,7,11-trien-1-yl)-1,3-dioxolane | 2-methyl-2-((3E,7E)-4,8,12-trimethyl-trideca-3,7-dien-1-yl)-1,3-dioxolane | 2-methyl-2-((3Z,7Z)-4,8,12-trimethyl-trideca-3,7-dien-1-yl)-1,3-dioxolane |
| Yield [%] | 85 | 99 | Not determined |

Characterization Data

(E)-2-(4,8-dimethylnon-3-en-1-yl)-2-methyl-1,3-dioxolane (E-DHGA-en)

$^1$H NMR (300 MHz, CDCl$_3$) 5.12 (t, 1H), 3.95 (m, 4H), 2.2-2 (m, 2H), 1.94 (t, 2H), 1.8-1.3 (m, 11H), 1.2-1.0 (m, 2H), 0.87 (d, 6H) ppm.

(Z)-2-(4,8-dimethylnon-3-en-1-yl)-2-methyl-1,3-dioxolane (Z-DHGA-en)

$^1$H NMR (300 MHz, CDCl$_3$) δ 5.12 (t, 1H), 3.94 (m, 4H), 2.15-1.9 (m, 4H), 1.7-1.45 (m, 6H), 1.44-1.27 (m, 5H), 1.23-1.08 (m, 2H), 0.88 (d, 6H) ppm.

2-methyl-2-((3E,7E)-4,8,12-trimethyltrideca-3,7,11-trien-1-yl)-1,3-dioxolane (EE-FA-en)

$^1$H NMR (300 MHz, CDCl$_3$) δ 5.12 (m, 3H), 3.95 (m, 4H), 2.16-1.92 (m, 10H), 1.73-1.56 (m, 14H), 1.34 (s, 3H) ppm.

2-methyl-2-((3E,7E)-4,8,12-trimethyltrideca-3,7-dien-1-yl)-1,3-dioxolane (EE-DHFA-en)

$^1$H NMR (300 MHz, CDCl$_3$) δ 5.18-5.08 (m, 2H), 3.99-3.91 (m, 4H), 2.16-1.05 (m, 24H), 0.95-0.80 (d, 6H) ppm.

2-methyl-2-((3Z,7Z)-4,8,12-trimethyltrideca-3,7,11-trien-1-yl)-1,3-dioxolane (ZZ-DHFA-en)

$^1$H NMR (300 MHz, CDCl$_3$) δ 5.13 (m, 3H), 3.94 (m, 4H), 2.2-1.9 (m, 10H), 1.73-1.5 (m, 14H), 1.33 (s, 3H) ppm.

c) Preparation of Neopentyl Glycol Ketals

The ketone (90.7 mmol) indicated in tables 1f or 1g, 2,2-dimethyl-1,3-propanediol (neopentylglycol, 32.4 g, 283 mmol, 3.4 eq.) and p-toluene sulfonic acid monohydrate (60 mg, 0.31 mmol, 0.3 mol %) were suspended in toluene (300 mL). The reaction was heated to 90° C. upon which a homogeneous solution formed. Subsequently, at 75° C., vacuum was applied cautiously (first 63 mbar, then 24 mbar) in order to slowly distill toluene off (approx. 100 mL over 4 h). After 4 h, thin layer chromatography (TLC) analysis indicated full conversion of the ketone. The reaction was allowed to cool to room temperature and diluted with heptane (300 mL) upon which excess neopentylglycol precipitated. The precipitate was filtered off (17.4 g wet). The filtrate was treated with Et$_3$N (1 mL), subsequently washed with aqueous NaHCO$_3$ solution (2.4% w/w, 2×300 mL), dried over MgSO$_4$ and concentrated in vacuo. The crude product was purified by distillation, furnishing the desired neopentyl ketal. the characterization of which is given in detail hereafter.

TABLE 1f

Preparation of neopentyl glycol ketals of 6,10-dimethylundeca-5,9-dien-2-one and 6,10-dimethylundec-5-en-2-one.

| | E-GA-neo | Z-GA-neo | E-DHGA-neo | Z-DHGA-neo |
|---|---|---|---|---|
| Ketone | (E)-6,10-dimethyl-undeca-5,9-dien-2-one | (Z)-6,10-dimethyl-undeca-5,9-dien-2-one | (E)-6,10-dimethyl-undec-5-en-2-one | (Z)-6,10-dimethyl-undec-5-en-2-one |
| Ketal | (E)-2-(4,8-dimethyl-nona-3,7-dien-1-yl)-2,5,5-trimethyl-1,3-dioxane | (Z)-2-(4,8-dimethyl-nona-3,7-dien-1-yl)-2,5,5-trimethyl-1,3-dioxane | (E)-2-(4,8-dimethyl-non-3-en-1-yl)-2,5,5-trimethyl-1,3-dioxane | (Z)-2-(4,8-dimethyl-non-3-en-1-yl)-2,5,5-trimethyl-1,3-dioxane |
| Yield [%] | 78 | 87 | 89 | 84 |
| E/Z | 99.4/0.6 | 1.7/98.3 | 95.3/4.7 | 1.6/98.4 |

TABLE 1g

Preparation of neopentyl glycol ketals of 6,10,14-trimethylpentadeca-5,9-dien-2-one and (R)-6,10,14-trimethylpentadec-5-en-2-one.

| | EE-DHFA-neo | ZZ-DHFA-neo | R,E-THFA | R,Z-THFA |
|---|---|---|---|---|
| Ketone | (5E,9E)-6,10,14-trimethyl-pentadeca-5,9-dien-2-one | (5Z,9Z)-6,10,14-trimethyl-pentadeca-5,9-dien-2-one | (R,E)-6,10,14-trimethyl-pentadec-5-en-2-one | (R,Z)-6,10,14-trimethyl-pentadec-5-en-2-one |
| Ketal | 2,5,5-trimethyl-2-((3E,7E)-4,8,12-trimethyl-trideca-3,7-dien-1-yl)-1,3-dioxane | 2,5,5-trimethyl-2-((3Z,7Z)-4,8,12-trimethyl-trideca-3,7-dien-1-yl)-1,3-dioxane | (R,E)-2,5,5-trimethyl-2-(4,8,12-trimethyl-tridec-3-en-1-yl)-1,3-dioxane | (R,Z)-2,5,5-trimethyl-2-(4,8,12-trimethyl-tridec-3-en-1-yl)-1,3-dioxane |
| Yield [%] | 81 | 70 | 83 | 86 |
| EE/(ZE + ZE)/ZZ | 97.0/3.0/0.0 | 0.0/2.5/97.5 | | |
| E/Z | | | 99.8/0.2 | 4/96 |

Characterization Data

(E)-2-(4,8-dimethylnona-3,7-dien-1-yl)-2,5,5-trimethyl-1,3-dioxane (E-GA-neo)

$^1$H NMR (300 MHz, CDCl$_3$): δ 0.92 (s, 3H), 0.99 (s, 3H), 1.37 (s, 3H), 1.59 (s, 3H), 1.61 (s, 3H), 1.67 (s, 3H), 1.68-1.75 (m, 2H), 1.94-2.15 (m, 6H), AB signal ($δ_A$=3.46, $δ_B$=3.52, $J_{AB}$=11.3 Hz, 4H), 5.05-5.17 (m, 2H) ppm.

$^{13}$C NMR (75 MHz, CDCl$_3$): δ 15.9 (1C), 17.6 (1C), 20.8 (1C), 22.0 (1C), 22.6 (1C), 22.7 (1C), 25.6 (1C), 26.7 (1C), 29.9 (1C), 37.3 (1C), 39.6 (1C), 70.3 (2C), 98.8 (1C), 124.1 (1C), 124.3 (1C), 131.2 (1C), 135.1 (1C) ppm.

MS (EI, m/z): 280 (M+, 3), 265 [(M-CH$_3$)$^+$, 14], 176 (21), 129 [(C$_7$H$_{13}$O$_2$)$^+$, 100], 69 (63), 43 (43).

IR (cm$^{-1}$): 2954 (m), 2925 (m), 2858 (m), 2731 (w), 1720 (w), 1669 (w), 1473 (w), 1450 (m), 1394 (m), 1372 (m), 1349 (w), 1306 (w), 1271 (w), 1249 (m), 1211 (m), 1186 (m), 1123 (s), 1088 (s), 1043 (m), 1021 (m), 984 (w), 950 (w), 925 (w), 907 (w), 862 (m), 837 (w), 792 (w), 742 (w), 677 (w), 667 (w).

(Z)-2-(4,8-dimethylnona-3,7-dien-1-yl)-2,5,5-trimethyl-1,3-dioxane (Z-GA-neo)

$^1$H NMR (300 MHz, CDCl$_3$): δ 0.91 (s, 3H), 0.97 (s, 3H), 1.35 (s, 3H), 1.60 (s, 3H), 1.64-1.74 (m, 5H) superimposed by 1.67 (br s, 3H), 1.99-2.18 (m, 6H), AB signal ($δ_A$=3.44, $δ_B$=3.51, $J_{AB}$=11.3 Hz, 4H), 5.07-5.16 (m, 2H) ppm.

$^{13}$C NMR (75 MHz, CDCl$_3$): δ 17.5 (1C), 20.9 (1C), 21.3 (1C), 21.9 (1C), 22.5 (1C), 22.6 (1C), 23.3 (1C), 25.7 (1C), 26.6 (1C), 29.9 (1C), 31.8 (1C), 37.5 (1C), 70.3 (1C), 98.7 (1C), 124.3 (1C), 124.9 (1C), 131.4 (1C), 135.2 (1C) ppm.

MS (EI, m/z): 280 (M+, 3), 265 [(M-CH$_3$)$^+$, 13], 176 (19), 129 [(C$_7$H$_{13}$O$_2$)$^+$, 100], 107 (15), 69 (62), 43 (39).

IR (cm$^{-1}$): 2954 (m), 2927 (m), 2858 (m), 2729 (w), 1721 (w), 1671 (w), 1473 (m), 1450 (m), 1394 (m), 1374 (m), 1349 (w), 1315 (w), 1271 (m), 1249 (m), 1211 (m), 1187 (m), 1149 (w), 1120 (s), 1086 (s), 1043 (m), 1021 (m), 985 (w), 951 (m), 925 (w), 907 (m), 857 (m), 833 (m), 792 (w), 743 (w), 677 (w), 667 (w).

(E)-2-(4,8-dimethylnon-3-en-1-yl)-2,5,5-trimethyl-1,3-dioxane (E-DHGA-neo)

$^1$H NMR (300 MHz, CDCl$_3$): δ 0.87 (d, J=6.6 Hz, 6H), 0.93 (s, 3H), 1.00 (s, 3H), 1.06-1.22 (m, 2H), 1.31-1.43 (m, 2H) superimposed by 1.38 (s, 3H), 1.53 (tqq, J=6.6, 6.6, 6.6 Hz, 1H), 1.61 (br s, 3H), 1.65-1.77 (m, 2H), 1.94 (t, J=7.5 Hz, 2 H), 2.05-2.17 (m, 2H), AB signal (δ$_A$=3.46, δ$_B$=3.54, J$_{AB}$=11.4 Hz, 4H), 5.13 (tq, J=7.1, 1.1 Hz, 1H) ppm.
$^{13}$C NMR (75 MHz, CDCl$_3$): δ 15.8 (1C), 20.9 (1C), 22.0 (1C), 22.59 (1C), 22.63 (2C), 22.7 (1C), 25.7 (1C), 27.9 (1C), 29.9 (1C), 37.3 (1C), 38.6 (1C), 39.9 (1C), 70.3 (2C), 98.8 (1C), 123.8 (1C), 135.6 (1C) ppm.

MS (EI, m/z): 282 (M+, 5), 267 [(M-CH$_3$)$^+$, 10], 129 (100), 95 (14), 69 (36), 43 (32).

IR (cm$^{-1}$): 2953 (s), 2929 (m), 2868 (m), 1720 (w), 1468 (m), 1394 (m), 1381 (m), 1368 (m), 1349 (w), 1306 (w), 1270 (w), 1250 (m), 1211 (m), 1187 (w), 1118 (s), 1087 (s), 1066 (m), 1044 (m), 1022 (m), 950 (m), 925 (w), 907 (m), 862 (m), 791 (w), 739 (w), 677 (w), 666 (w).

(Z)-2-(4,8-dimethylnon-3-en-1-yl)-2,5,5-trimethyl-1,3-dioxane (Z-DHGA-neo)

$^1$H NMR (300 MHz, CDCl$_3$): δ 0.87 (d, J=6.6 Hz, 6H), 0.93 (s, 3H), 0.97 (s, 3H), 1.10-1.20 (m, 2H), 1.34-1.41 (m, 3H) superimposed by 1.36 (s, 3H), 1.53 (tqq, J=6.6, 6.6, 6.6 Hz, 1H), 1.64-1.75 (m, 2H) superimposed by 1.67 (q, J=1.5 Hz, 3H), 1.95-2.15 (m, 4H), AB signal (δ$_A$=3.46, δ$_B$=3.51, J$_{AB}$=11.1 Hz, 4H), 5.12 (br t, J=7.2 Hz, 1H)
$^{13}$C NMR (75 MHz, CDCl$_3$): δ 21.1 (1C), 22.0 (1C), 22.61 (3C), 22.65 (1C), 23.4 (1C), 25.7 (1C), 27.9 (1C), 29.9 (1C), 31.9 (1C), 37.2 (1C), 38.8 (1C), 70.3 (2 C), 98.8 (1C), 124.6 (1C), 135.8 (1C) ppm.

MS (EI, m/z): 282 (M, 6), 267 [(M-CH$_3$)$^+$, 11], 129 (100), 95 (14), 69 (35), 43 (32).

IR (cm$^{-1}$): 2953 (s), 2867 (m), 1722 (w), 1468 (m), 1394 (m), 1368 (m), 1349 (w), 1306 (w), 1270 (w), 1250 (m), 1211 (m), 1189 (w), 1116 (s), 1086 (s), 1043 (m), 1022 (m), 951 (m), 925 (w), 907 (m), 856 (m), 792 (w), 739 (w), 677 (w), 667 (w).

2,5,5-trimethyl-2-((3E,7E)-4,8,12-trimethyltrideca-3,7-dien-1-yl)-1,3-dioxane (EE-DHFA-neo)

$^1$H NMR (300 MHz, CDCl$_3$): δ 0.86 (d, J=6.6 Hz, 6H), 0.92 (s, 3H), 0.99 (s, 3H), 1.05-1.22 (m, 2H), 1.37 (s, 3H), superimposed by 1.31-1.42 (m, 2H), 1.52 (tqq, J=6.6, 6.6, 6.6 Hz, 1H), 1.57 (s, 3H), 1.61 (s, 3H), 1.67-1.76 (m, 2H), 1.88-2.16 (m, 8H), AB signal (δ$_A$=3.45, δ$_{8B}$=3.52, J$_{AB}$=11.3 Hz, 4H), 5.05-5.17 (m, 2H) ppm.
$^{13}$C NMR (75 MHz, CDCl$_3$): δ 15.85 (1C), 15.92 (1C), 20.9 (1C), 22.0 (1C), 22.55 (1C), 22.62 (2C), 22.68 (1C), 25.7 (1C), 26.5 (1C), 27.8 (1C), 29.9 (1C), 37.3 (1C), 38.6 (1C), 39.7 (1C), 39.9 (1C), 70.3 (2C), 98.8 (1C), 123.9 (1C), 124.1 (1C), 135.1 (1C), 135.2 (1C) ppm.

MS (EI, m/z): 350 (M+, 4), 335 [(M-CH$_3$)$^+$, 11), 246 (10), 206 (10), 161 (9), 129 (100), 107 (13), 69 (38), 43 (32).

IR (cm$^{-1}$): 2953 (s), 2928 (s), 2867 (m), 1462 (m), 1394 (m), 1382 (m), 1368 (m), 1305 (w), 1271 (w), 1249 (m), 1211 (m), 1187 (m), 1123 (s), 1087 (s), 1043 (m), 1021 (m), 950 (w), 925 (w), 907 (w), 862 (m) 791 (w), 739 (w), 678 (w).

2,5,5-trimethyl-2-((3E,7E)-4,8,12-trimethyltrideca-3,7-dien-1-yl)-1,3-dioxane (ZZ-DHFA-neo)

$^1$H NMR (300 MHz, CDCl$_3$): δ 0.87 (d, J=6.8 Hz, 6H), 0.92 (s, 3H), 0.98 (s, 3H), 1.10-1.21 (m, 2H), 1.29-1.42 (m, 2H), superimposed by 1.36 (s, 3H), 1.53 (qqt, J=6.7, 6.7, 6.7 Hz, 1H), 1.66 (br. s, 3H), 1.68 (q, J=1.4 Hz, 3H), 1.67-1.75 (m, 2H), 1.99 (t, J=7.7 Hz, 2H), 2.02-2.16 (m, 6H), AB signal (δ$_A$=3.45, δ$_8$=3.52, J$_{AB}$=11.5 Hz, 4H), 5.02-5.22 (m, 2H) ppm.
$^{13}$C NMR (75 MHz, CDCl$_3$): δ 20.9 (1C), 21.9 (1C), 22.6 (3C), 22.7 (1C), 23.38 (1C), 23.42 (1C), 25.8 (1C), 26.3 (1C), 27.9 (1C), 29.9 (1C), 31.9 (1C), 32.1 (1C), 37.4 (1C), 38.9 (1C), 70.3 (2C), 98.8 (1C), 124.7 (1C), 125.0 (1C), 135.2 (1C), 135.6 (1C) ppm.

MS (EI, m/z): 350 (M+, 5), 335 [(M-CH$_3$)$^+$, 10), 246 (8), 206 (8), 151 (7), 129 (100), 107 (10), 69 (35), 43 (27).

IR (cm$^{-1}$): 2953 (s), 2867 (m), 1452 (m), 1394 (w), 1372 (m), 1315 (w), 1271 (w), 1249 (m), 1211 (m), 1189 (w), 1119 (s), 1087 (s), 1043 (m), 1021 (m), 951 (w), 925 (w), 907 (w), 856 (m) 792 (w), 737 (w), 668 (w).

(R,E)-2,5,5-trimethyl-2-(4,8,12-trimethyltridec-3-en-1-yl)-1,3-dioxane (R,E-THFA)

$^1$H NMR (300 MHz, CDCl$_3$): δ 0.84 (d, J=6.4 Hz, 3H), 0.86 (d, J=6.6 Hz, 6H), 0.92 (s, 3H), 0.99 (s, 3H), superimposed by 0.97-1.44 (m, 11H), superimposed by 1.37 (s, 3H), 1.52 (qqt, J=6.9, 6.9, 6.9 Hz, 1H), 1.60 (s, 3H), 1.67-1.76 (m, 2H), 1.93 (t, J=7.4 Hz, 2H), 2.03-2.18 (m, 2H), AB signal (δ$_A$=3.45, δ$_{8B}$=3.52, J$_{AB}$=11.4 Hz, 4H), 5.12 (tq, J=7.2, 1.0 Hz, 1H) ppm.
$^{13}$C NMR (75 MHz, CDCl$_3$): δ 15.8 (1C), 19.7 (1C), 20.9 (1C), 22.0 (1C), 22.6 (2C), 22.7 (2C), 24.8 (1C), 25.3 (1C), 27.9 (1C), 29.9 (1C), 32.6 (1C), 36.6 (1C), 37.3 (1C), 37.4 (1C), 39.3 (1C), 39.9 (1C), 70.3 (2C), 98.8 (1C), 123.8 (1C), 135.5 (1C) ppm.

MS (EI, m/z): 352 (M+, 4), 337 [(M-CH$_3$)$^+$, 8), 265 (6), 129 (100), 95 (10), 69 (25), 43 (25).

IR (cm$^{-1}$): 2953 (s), 2926 (s), 2867 (m), 1462 (m), 1394 (w), 1369 (m), 1270 (w), 1249 (m), 1211 (m), 1187 (w), 1119 (s), 1088 (s), 1043 (m), 1021 (m), 951 (w), 925 (w), 907 (w), 862 (m), 791 (w), 738 (w), 678 (w).

(R,Z)-2,5,5-trimethyl-2-(4,8,12-trimethyltridec-3-en-1-yl)-1,3-dioxane (R,Z-THFA)

$^1$H NMR (300 MHz, CDCl$_3$): δ 0.84 (d, J=6.4 Hz, 3H), superimposed by 0.86 (d, J=6.6 Hz, 6H), 0.93 (s, 3H), 0.97 (s, 3H), 1.00-1.42 (m, 11H), superimposed by 1.36 (s, 3H), 1.52 (qqt, J=6.7, 6.7, 6.7 Hz, 1H), 1.63-1.76 (m, 2H), 1.67 (s, 3H), 1.94-2.15 (m, 4H), AB signal (δ$_A$=3.45, δ$_B$=3.51, J$_{AB}$=11.1 Hz, 4H), 5.12 (t, J=7.1 Hz, 1H) ppm.
$^{13}$C NMR (75 MHz, CDCl$_3$): δ 19.6 (1C), 21.1 (1C), 21.9 (1C), 22.60 (2C), 22.67 (2C), 22.69 (1C), 23.4 (1C), 24.8 (1C), 25.4 (1C), 27.9 (1C), 29.9 (1C), 32.0 (1C), 32.7 (1C), 36.9 (1C), 37.3 (1C), 39.3 (1C), 70.3 (2C), 98.8 (1C), 124.6 (1C), 135.7 (1C) ppm.

MS (EI, m/z): 352 (M+, 3), 337 [(M-CH$_3$)$^+$, 9), 265 (6), 129 (100), 95 (10), 69 (24), 43 (25).

IR (cm$^{-1}$): 2953 (s), 2926 (s), 2860 (m), 1463 (m), 1394 (w), 1371 (m), 1270 (w), 1250 (w), 1211 (m), 1188 (w), 1117 (s), 1086 (s), 1043 (m), 1022 (w), 951 (w), 925 (w), 907 (w), 855 (m), 792 (w), 737 (w), 667 (w).

d) Preparation of Bis(Trifluoroethyl) Ketals

A 250 mL three-necked flask with stir bar was dried under high vacuum (heat gun at 250° C.), then allowed to cool, flushed with argon and charged with 1,1,1 trifluoroethanol (TFE) (40 mL) under argon. The flask was cooled with an ice-bath while trimethylaluminum (2 M in heptane, 20.0 mL, 40.0 mmol, 1.95 eq.) was added dropwise within 60 min, keeping the temperature below 22° C. The two-phase (TFE/heptane) mixture became clear again after a few minutes and was allowed to stir for an additional 20 min at room temperature. 20.7 mmol of the dimethyl ketal of the corresponding ketone as indicated in tables 1h or 1i, being prepared as shown above, was added dropwise within 5 min at room temperature. After 1.5 h, GC analysis indicated full conversion of starting material. The reaction was quenched with a half-saturated solution of potassium sodium tartrate in water (100 mL), stirred for 2 h at room temperature and finally diluted with n-hexane (200 mL). The organic phase was separated, extracted with n-hexane (2×100 mL), dried over MgSO$_4$ and concentrated. The crude product was purified by column chromatography (neutral aluminium oxide, eluent: n-hexane). The characterization of the ketal is given in detail hereafter.

TABLE 1h

Preparation of bis(trifluoroethyl) ketals of 6,10-dimethylundeca-5,9-dien-2-one and 6,10-dimethylundec-5-en-2-one.

| | E-GA-tfe | E-DHGA-tfe |
|---|---|---|
| Dimethylketal (reactant) | E-GA-DM | E-DHGA-DM |
| Ketal | (E)-2,6-dimethyl-10,10-bis(2,2,2-trifluoroethoxy)undeca-2,6-diene | (E)-6,10-dimethyl-2,2-bis(2,2,2-trifluoroethoxy)undec-5-ene |
| Yield [%] | 85 | 74 |
| E/Z | 99.4/0.6 | 95.0/5.0 |

TABLE 1i

Preparation of bis(trifluoroethyl) ketals of (5E,9E)-6,10,14-trimethyl-pentadeca-5,9,13-trien-2-one and (5E,9E)-6,10,14-trimethylpenta-deca-5,9-dien-2-one.

| | EE-FA-tfe | EE-DHFA-tfe |
|---|---|---|
| Dimethylketal (reactant) | (6E,10E)-14,14-dimethoxy-2,6,10-trimethylpentadeca-2,6,10-triene | (5E,9E)-2,2-dimethoxy-6,10,14-trimethylpentadeca-5,9-diene |
| Ketal | (6E,10E)-2,6,10-trimethyl-14,14-bis(2,2,2-trifluoro-ethoxy)-pentadeca-2,6,10-triene | (5E,9E)-6,10,14-trimethyl-2,2-bis(2,2,2-trifluoro-ethoxy)pentadeca-5,9-diene |
| Yield [%] | 71 | 83 |
| EE/(ZE + ZE + ZZ) | 99/1 | 95/5 |

Characterization Data (E)-2,6-dimethyl-10,10-bis(2,2,2-trifluoroethoxy)undeca-2,6-diene (E-GA-tfe)

$^1$H NMR (300 MHz, CDCl$_3$): δ 1.41 (s, 3H), 1.62 (br s, 6H), 1.67-1.76 (m, 2H), superimposed by 1.69 (q, J=0.9 Hz, 3H), 1.93-2.15 (m, 6H), 3.73-3.97 (m, 4H), 5.02-5.18 (m, 2H) ppm.

$^{13}$C NMR (150 MHz, CDCl$_3$): δ 15.9 (1C), 17.6 (1C), 21.3 (1C), 22.6 (1C), 25.7 (1C), 26.6 (1C), 36.9 (1C), 39.6 (1C), 59.3 (q, J$_{C,F}$=35.0 Hz, 2C), 103.4 (1C), 124.0 (q, J$_{C,F}$=275.0 Hz, 2C), 122.7 (1C), 124.1 (1C), 131.5 (1C), 136.2 (1C) ppm.

MS (EI, m/z): 361 [(M-CH$_3$)$^+$, 1], 276 [(M-TFE)$^+$, 15], 225 [(CF$_3$CH$_2$O)$_2$C—CH$_3$)$^+$, 86], 207 (20), 153 (18), 136 (58), 107 (80), 69 (100), 41 (40).

IR (cm$^{-1}$): 2927 (w), 2859 (w), 1459 (w), 1419 (w), 1385 (w), 1281 (s), 1223 (w), 1156 (s), 1133 (s), 1081 (s), 971 (s), 889 (m), 860 (w), 845 (w), 678 (w), 663 (w).

(E)-6,10-dimethyl-2,2-bis(2,2,2-trifluoroethoxy) undec-5-ene (E-DHGA-tfe)

$^1$H NMR (600 MHz, CDCl$_3$): δ 0.88 (d, J=6.8 Hz, 6H), 1.11-1.17 (m, 2H), 1.35-1.40 (m, 2H), 1.41 (s, 3H), 1.54 (qqt, J=6.7, 6.7, 6.7 Hz, 1H), 1.61 (br s, 3H), 1.69-1.73 (m, 2H), 1.95 (t, J=7.7 Hz, 2H), 2.03-2.09 (m, 2H), 3.78-3.91 (m, 4H), 5.09 (tq, J=7.1, 1.3 Hz, 1H) ppm.

$^{13}$C NMR (151 MHz, CDCl$_3$): δ 14.1 (1C), 15.8 (1C), 21.3 (1C), 22.56 (1C), 22.61 (1C), 25.6 (1C), 27.9 (1C), 37.0 (1C), 38.6 (1C), 39.8 (1C), 59.2 (q, J$_{C,F}$=35.0 Hz, 2C), 103.4 (1C), 124.0 (q, J$_{C,F}$=277.0 Hz, 2C), 122.4 (1C), 136.7 (1C) ppm.

MS (EI, m/z): 363 [(M-CH$_3$)$^+$, 1], 278 [(M-TFE)$^+$, 22], 225 [(CF$_3$CH$_2$O)$_2$C—CH$_3$)$^+$, 60], 193 (100), 153 (13), 127 (11), 83 (CF$_3$CH$_2^+$, 25), 69 (13), 43 (17).

IR (cm$^{-1}$): 2956 (w), 2933 (w), 2872 (w), 1462 (w), 1419 (w), 1385 (w), 1368 (w), 1281 (s), 1223 (w), 1156 (s), 1134 (s), 1081 (s), 971 (s), 889 (m), 860 (w), 845 (w), 679 (w), 663 (m).

(6E,10E)-2,6,10-trimethyl-14,14-bis(2,2,2-trifluoroethoxy)pentadeca-2,6,10-triene (EE-FA-tfe)

$^1$H NMR (300 MHz, CDCl$_3$): δ 1.41 (s, 3H), 1.61 (br s, 6H), 1.63 (br s, 3H), 1.67-1.75 (m, 2H), superimposed by 1.69 (br q, J=0.9 Hz, 3H), 1.93-2.16 (m, 10H), 3.74-3.95 (m, 4H), 5.11 (br t, J=6.5 Hz, 3H) ppm.

$^{13}$C NMR (75 MHz, CDCl$_3$): δ 15.94 (1C), 15.98 (1C), 17.6 (1C), 21.3 (1C), 22.6 (1C), 25.6 (1C), 26.5 (1C), 26.8 (1C), 37.0 (1C), 39.6 (1C), 39.7 (1C), 59.3 (q, J$_{C,F}$=34.9 Hz, 2C), 103.4 (1C), 124.0 (q, J$_{C,F}$=275.8 Hz, 2C), 122.7 (1C), 124.0 (1C), 124.3 (1C), 131.3 (1C), 135.1 (1C), 136.2 (1C) ppm.

MS (EI, m/z): 444 (M+, 5), 429 [(M-CH$_3$)$^+$, 1], 344 [(M-TFE)$^+$, 4], 225 [(CF$_3$CH$_2$O)$_2$C—CH$_3$)$^+$, 54], 175 (33), 136 (28), 107 (48), 81 (53), 69 (100), 41 (34).

IR (cm$^{-1}$): 2922 (w), 2858 (w), 1457 (w), 1419 (w), 1385 (w), 1282 (s), 1223 (w), 1157 (s), 1133 (s), 1111 (m), 1081 (s), 971 (s), 889 (m), 860 (w), 845 (w), 678 (w), 663 (m).

(5E,9E)-6,10,14-trimethyl-2,2-bis(2,2,2-trifluoroethoxy)pentadeca-5,9-diene (EE-DHFA-tfe)

$^1$H NMR (300 MHz, CDCl$_3$): δ 0.88 (d, J=6.6 Hz, 6H), 1.08-1.20 (m, 2H), 1.32-1.44 (m, 2H), superimposed by 1.41

(s, 3H), 1.54 (tqq, J=6.6, 6.6, 6.6 Hz, 1H), 1.60 (br s, 3H), 1.63 (br s, 3H), 1.67-1.76 (m, 2H), 1.89-2.17 (m, 8H), 3.73-3.97 (m, 4H), 5.04-5.17 (m, 2H) ppm.

$^{13}$C NMR (75 MHz, CDCl$_3$): δ 15.89 (1C), 15.95 (1C), 21.4 (1C), 22.60 (1C), 22.61 (2C), 25.8 (1C), 26.5 (1C), 27.9 (1C), 37.0 (1C), 38.6 (1C), 39.7 (1C), 39.9 (1C), 59.3 (q, $J_{C,F}$=35.5 Hz, 2C), 103.4 (1C), 124.0 (q, $J_{C,F}$=276.0 Hz, 2C), 122.7 (1C), 123.7 (1C), 135.5 (1C), 136.2 (1C) ppm.

MS (EI, m/z): 431 [(M-CH$_3$)$^+$, 1], 346 [(M-TFE)$^+$, 13], 262 (9), 225 [(CF$_3$CH$_2$O)$_2$C—CH$_3$)$^+$, 93], 206 (43), 153 (17), 127 (24), 107 (45), 83 (CF$_3$CH$_2^+$, 100), 69 (51), 55 (43), 43 (28).

IR (cm$^{-1}$): 2955 (w), 2931 (w), 2871 (w), 1462 (w), 1419 (w), 1385 (m), 1282 (s), 1223 (w), 1157 (s), 1133 (s), 1080 (s), 971 (s), 889 (m), 860 (w), 845 (w), 679 (w), 663 (m).

Experiment E2

Preparation of Acetals of Unsaturated Aldehydes (E)-3,7-dimethylocta-2,6-dienal (geranial) was separated from citral, a mixture of geranial and neral by distillation.

Formation of neopentyl glycol ketals of (E)-3,7-dimethylocta-2,6-dienal (Geranial-neo)

Tetramethyl orthocarbonate (0.675 g, 4.86 mmol, 98%, 1.48 eq.) was suspended in dichloromethane (10 mL) under argon at room temperature. 2,2-Dimethylpropane-1,3-diol (2.27 g, 21.8 mmol, 6.6 eq.) was added and the mixture was stirred for 2 h, after which a clear solution was obtained. Boron trifluoride etherate (0.372 mL, 0.422 g, 2.88 mmol, 97%, 0.90 eq.) was added and after stirring for 10 min at room temperature, the reaction was cooled to −78° C. The reaction was diluted with dichloromethane (5 mL) and geranial (0.503 g, 3.29 mmol, 99.9%, 1.0 eq., (Aug. 10, 2012)) was added slowly and dropwise via a cooled syringe (using dry ice wrapped in a towel) over 10 min. Subsequently, the reaction was stirred at −78° C. or 1 h. GC analysis indicated full conversion. The reaction was quenched slowly with cooled triethylamine (4.0 mL, 2.91 g, 28.7 mmol, 8.7 eq.) at −78° C. Subsequently, sat. aq. NaHCO$_3$ (6 mL) was added at −78° C. and the suspension was allowed to warm to room temperature. The reaction was diluted with pentane (50 mL) and the organic phase was washed with sat. aq. NaHCO$_3$ (2×50 mL), water (50 mL), dried over MgSO$_4$, filtered and concentrated in vacuo, furnishing (E)-2-(2,6-dimethylhepta-1,5-dien-1-yl)-5,5-dimethyl-1,3-dioxane (573 mg, 97.3% (GC), 71% yield, E/Z 97.6:2.4) as colorless liquid.

Characterization Data of (E)-2-(2, 6-dimethylhepta-1,5-dien-1-yl)-5,5-dimethyl-1,3-dioxane (Geranial-neo)

$^1$H NMR (300 MHz, CDCl$_3$): δ 0.74 (s, 3H), 1.23 (s, 3H), 1.59 (s, 3H), 1.68 (s, 3H), 1.74 (d, J=1.3 Hz, 3H), 1.98-2.18 (m, 4H), AB signal (δ$_A$=3.51, δ$_B$=3.65, $J_{AB}$=11.0 Hz, 4H), 5.06-5.15 (m, 1H), 5.09 (d, J=6.4 Hz, 1H), 5.34 (dq, J=6.2, 1.1 Hz, 1H).

$^{13}$C NMR (75 MHz, CDCl$_3$): δ 17.3 (1C), 17.6 (1C), 21.9 (1C), 23.0 (1C), 25.6 (1C), 26.2 (1C), 30.0 (1C), 39.2 (1C), 77.3 (2C), 98.9 (1C), 121.7 (1C), 123.8 (1C), 131.8 (1C), 142.9 (1C) ppm.

MS (EI, m/z): 238 (M+, 7), 237 [(M-H)$^+$, 7], 223 [(M-CH$_3$)$^+$, 5], 195 (15), 181 (6), 169 (30), 134 (12), 115 (30), 83 (26), 69 (100), 55 (30), 41 (57).

IR (cm$^{-1}$): 2953 (w), 2928 (w), 2845 (w), 1746 (w), 1680 (w), 1451 (w), 1393 (m), 1362 (w), 1305 (w), 1258 (w), 1232 (w), 1192 (w), 1142 (m), 1093 (s), 1041 (w), 1015 (m), 981 (s), 967 (s), 929 (m), 814 (w), 790 (w), 670 (w).

(E)-1,1-dimethoxy-3,7-dimethylocta-2,6-diene (Geranial-DM)

$^1$H NMR (300 MHz, CDCl$_3$): δ 1.60 (s, 3H), 1.67 (d, J=0.9 Hz, 3H), 1.72 (d, J=1.1 Hz, 3H), 2.01-2.17 (m, 4H), 3.30 (s, 6H), 5.03 (d, J=6.4 Hz, 1H), 5.09 (tqq, J=6.8, 1.3 Hz, 1H), 5.24 (dq, J=6.4, 1.3 Hz, 1H) ppm.

$^{13}$C NMR (75 MHz, CDCl$_3$): δ 17.4 (s, 1C), 18.0 (s, 1C), 26.0 (s, 1C), 26.6 (s, 1C), 39.8 (s, 1C), 52.5 (s, 2C), 100.8 (s, 1C), 122.0 (s, 1C), 124.2 (s, 1C), 132.2 (s, 1C), 142.4 (s, 1C) ppm.

MS (EI, m/z): 198.2 (M+, 1), 183.2 [(M-CH$_3$)$^+$, 1], 167.2 [(M-CH$_3$O)$^+$, 19], 151.2 (11), 123.2 (25), 98.2 (37), 83.2 (47), 75.2 (50), 73.2 (70), 69.2 (100), 55.1 (23), 41.1 (53).

IR (cm$^{-1}$) 2927 (w), 2827 (w), 1672 (w), 1443 (w), 1378 (w), 1212 (w), 1190 (w), 1130 (s), 1109 (m), 1078 (m), 1050 (s), 962 (m), 907 (m), 829 (w).

(Z)-1,1-dimethoxy-3,7-dimethylocta-2,6-diene (Neral-DM)

$^1$H NMR (300 MHz, CDCl$_3$): δ 1.59 (s, 3H), 1.66 (s, 3H), 1.74 (d, J=1.3 Hz, 3H), 2.03-2.14 (m, 4H), 3.28 (s, 6H), 4.99 (d, J=6.8 Hz, 1H), 5.05-5.14 (m, 1H), 5.24 (dd, J=6.8, 1.3 Hz, 1H) ppm.

$^{13}$C NMR (75 MHz, CDCl$_3$): δ 17.6 (1C), 23.2 (1C), 25.6 (1C), 26.5 (1C), 32.7 (1C), 52.3 (2C), 100.2 (1C), 122.6 (1C), 123.8 (1C), 131.9 (1C), 142.1 (1C) ppm.

MS (EI, m/z): 198.2 (M+, 6), 183.2 [(M-CH$_3$)$^+$, 6], 166.2 [(M-CH$_3$OH)$^+$, 7], 151.2 (25), 141.2 (29), 123.2 (45), 115.2 (25), 98.2 (43), 83.2 (83), 73.2 (85), 69.2 (100), 55.1 (38), 41.1 (84).

IR (cm$^{-1}$): 2915 (w), 2826 (w), 1672 (w), 1446 (m), 1377 (m), 1190 (w), 1145 (w), 1125 (m), 1105 (m), 1076 (m), 1050 (s), 963 (m), 907 (m), 829 (w), 747 (w).

Experiment E3

Asymmetric Hydrogenations of Ketals and Acetals

The ketals and acetals were asymmetrically hydrogenated in the following manner:

An autoclave vessel was charged under nitrogen with chiral iridium complex of formula as indicated in tables 2a-k having the configuration at the chiral centre marked by * as indicated in tables 2a-k, the ketal or acetal (conc.) as indicated in tables 2a-k, solvent as indicated in tables 2a-k. The reaction vessel was closed and pressurized with molecular hydrogen to the pressure (pH$_2$) indicated in tables 2a-k. The reaction mixture was stirred at room temperature for the time (t) as indicated in tables 2a-k under hydrogen. Then the pressure was released and the assay yield and the stereoisomer distribution of the fully hydrogenated product was determined. The catalyst loading (S/C) is defined as mmol ketal or acetal ("substrate")/mmol chiral iridium complex.

The characterization of the hydrogenated ketals/acetals is given hereafter.

TABLE 2a

|  | 1 | 2 | 3 | 4 |
|---|---|---|---|---|
| Ketal/ketone | E-GA | E-GA-DM | E-GA-neo | E-GA-neo |
| Formula of Ir complex | III-F | III-F | III-F | III-F |
| Configuration of chiral Ir complex at * | (S) | (S) | (S) | (S) |
| Amount of chiral Ir complex [mol-%] | 0.5 | 0.5 | 0.5 | 0.5 |
| Solvent[1] | DCM | TFE | DCM | TFE |
| Hydrogenated ketal/ketone | R-THGA | R-THGA-DM | R-THGA-neo | R-THGA-neo |
| Conversion [%] | 100 | >99 | >99 | >99 |
| Isomer-Distribution[2,3] | | | | |
| (R) [%] | 96.5 | 95.3 | 97.5 | 98.4 |
| (S) [%] | 3.5 | 4.7 | 2.5 | 1.6 |

Asymmetric hydrogenation of different ketals of E-6,10-dimethyl-undeca-5,9-dien-2-one (E-GA).
Conditions: 0.5 mmol ketal, 4 g solvent, pressure p(H$_2$) = 30 bar, 16 h stirring at room temperature.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 2b

|  | 5 | 6 | 7 | 8 |
|---|---|---|---|---|
| Ketal | Z-GA-DM | Z-GA-DM | Z-GA-neo | Z-GA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.25 | 0.25 | 0.25 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 98.2 | 98.5 | 97.9 | 98.6 |
| (S) [%] | 1.8 | 1.5 | 2.1 | 1.4 |

Asymmetric hydrogenation of different ketals of Z-6,10-dimethyl-undeca-5,9-dien-2-one (Z-GA).
Conditions: 0.5 mmol ketal, 4 g solvent, pressure p(H$_2$) = 30 bar, 16 h stirring at room temperature.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 2c

|  | 9 | 10 | 11 | 12 |
|---|---|---|---|---|
| Ketal | E-DHGA-DM | E-DHGA-DM | E-DHGA-neo | E-DHGA-tfe |
| Formula of Ir complex | III-F | III-F | III-F | III-F |
| Configuration of chiral Ir complex at * | (S) | (S) | (S) | (S) |
| Amount of chiral Ir complex [mol-%] | 0.25 | 0.5 | 0.25 | 0.5 |
| Solvent[1] | DCM | TFE | DCM | TFE |
| Hydrogenated ketal | R-THGA-DM | R-THGA-DM | R-THGA-neo | R-THGA-tfe |
| Conversion [%] | >99 | >99 | >99 | >99 |
| Isomer-Distribution[2,3] | | | | |
| (R) [%] | 93.8 | 94.3 | 94.7 | 94.8 |
| (S) [%] | 6.2 | 5.7 | 5.3 | 5.2 |

Asymmetric hydrogenation of different ketals of E-DHGA.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 2d

|  | 13 | 14 | 15 | 16 |
|---|---|---|---|---|
| Ketal | Z-DHGA-DM | Z-DHGA-DM | Z-DHGA-neo | Z-DHGA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.25 | 0.5 | 0.5 | 0.5 |
| Solvent[1] | DCM | TFE | DCM | TFE |
| Hydrogenated ketal | R-THGA-DM | R-THGA-DM | R-THGA-neo | R-THGA-neo |
| Conversion [%] | >99 | >99 | >99 | >99 |
| Isomer-Distribution[2,3] | | | | |
| (R) [%] | 99.2 | 99.4 | 97.8 | 98.0 |
| (S) [%] | 0.8 | 0.6 | 2.2 | 2.0 |

Asymmetric hydrogenation of different ketals of Z-DHGA.
[1]TFE = 2,2,2-trifluoroethanol; DCM = dichloromethane
[2](R) stands for the R-isomer, (S) stands for the S-isomer of the corresponding ketal of 6,10-dimethylundecan-2-one
[3]is determined as ketone after hydrolysis of the ketal

TABLE 2e

|  | 17 | 18 | 19 |
|---|---|---|---|
| Ketal to be hydrogenated | E,E-FA-DM | E,E-FA-DM | E,E-FA-tfe |
| Formula of Ir-complex | III-F | III-F | III-F |
| Configuration of chiral Ir-complex at * | (S) | (S) | (S) |
| Amount of chiral Ir complex [mol-%] | 0.25 | 0.25 | 0.5 |
| Solvent[1] | DCM | TFE | TFE |
| Conversion [%] | >99 | >99 | >99 |
| Isomer-Distribution[2,3] | | | |
| (RR) [%] | 97.1 | 96.4 | 96.5 |
| ((SS) + (RS)) [%] | 1.3 | 1.3 | 1.5 |
| (SR) [%] | 1.6 | 2.3 | 2.0 |

Asymmetric hydrogenation of different ketals of E,E-FA. Conditions: 0.5 mmol ketal, 4 g solvent, pressure p(H$_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal

TABLE 2f

|  | 20 | 21 | 22 | 23 | 24 |
|---|---|---|---|---|---|
| Ketal to be hydrogenated | E,E-DHFA-DM | E,E-DHFA-neo | E,E-DHFA-neo | Z,Z-DHFA-DM | Z,Z-DHFA-DM |

TABLE 2f-continued

|  | 20 | 21 | 22 | 23 | 24 |
|---|---|---|---|---|---|
| Formula of Ir-complex | III-F | III-F | III-F | III-F | III-F |
| Configuration of chiral Ir-complex at * | (S) | (S) | (S) | (R) | (R) |
| Amount of chiral Ir complex [mol-%] | 0.25 | 0.5 | 0.5 | 0.5 | 0.5 |
| Solvent[1] | DCM | DCM | TFE | DCM | TFE |
| Conversion [%] | >99 | >99 | >99 | >99 | >99 |
| Isomer-Distribution[2,3] | | | | | |
| (RR) [%] | 93.0 | 94.5 | 92.8 | 96.8 | 96.8 |
| ((SS) + (RS)) [%] | 5.5 | 5.5 | 5.9 | 1.4 | 1.6 |
| (SR) [%] | 1.5 | 0.0 | 1.3 | 1.7 | 1.6 |

Asymmetric hydrogenation of different ketals of E,E-DHFA and ZZ-DHFA. Conditions: 0.5 mmol ketal, 4 g solvent, pressure p($H_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethylpentadecan-2-one
[3]is determined as ketone after hydrolysis of the ketal

TABLE 2g

|  | 25 | 26 | 27 |
|---|---|---|---|
| Ketal to be hydrogenated | R-E-THFA-DM | R-E-THFA-DM | R-E-THFA-neo |
| Formula of Ir complex | III-F | III-F | III-F |
| Configuration of chiral Ir complex at * | (S) | (S) | (S) |
| Amount of chiral Ir complex [mol-%] | 0.25 | 0.25 | 0.5 |
| Solvent[1] | DCM | TFE | DCM |
| Conversion [%] | >99 | >99 | >99 |
| Isomer-Distribution[2,3] | | | |
| (RR) [%] | 90.0 | 88.7 | 90.6 |
| ((SS) + (RS)) [%] | 8.0 | 8.7 | 9.4 |
| (SR) [%] | 2.0 | 2.6 | 0.0 |

Asymmetric hydrogenation of different ketals of (R,E)-6,10,14-tri-methylpentadec-5-en-2-one leading to (6R,10R)-6,10,14-trimethyl-pentadecan-2-one. Conditions: 0.5 mmol ketal, 4 g solvent, pressure p($H_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethyl-pentadecan-2-one
[3]is determined as ketone after hydrolysis of the ketal

TABLE 2h

|  | 28 | 29 | 30 | 31 |
|---|---|---|---|---|
| Ketal to be hydrogenated | R-Z-THFA-DM | R-Z-THFA-DM | R-Z-THFA-neo | R-Z-THFA-neo |
| Formula of Ir complex | III-F | III-F | III-F | III-F |
| Configuration of chiral Ir complex at * | (R) | (R) | (R) | (R) |
| Amount of chiral Ir complex [mol-%] | 0.5 | 0.5 | 0.5 | 0.5 |
| Solvent[1] | DCM | TFE | DCM | TFE |
| Conversion [%] | >99 | >99 | >99 | >99 |
| Isomer-Distribution[2,3] | | | | |
| (RR) [%] | 86.3 | 87.4 | 86.8 | 85.5 |
| ((SS) + (RS)) [%] | 8.2 | 7.5 | 8.2 | 9.4 |
| (SR) [%] | 5.5 | 5.1 | 5.0 | 5.1 |

Asymmetric hydrogenation of different ketals of (R,Z)-6,10,14-tri-methylpentadec-5-en-2-one leading to (6R,10R)-6,10,14-trimethyl-pentadecan-2-one. Conditions: 0.5 mmol ketal, 4 g solvent, pressure p($H_2$) = 30 bar, 16 h stirring at room temperature
[1]TFE = 2,2,2-trifluoroethanol; DCM = dichloromethane
[2](SS) stands for the (6S,10S)-isomer, (RR) stands for the (6R,10R)-isomer, (SR) stands for the (6S,10R)-isomer, (RS) stands for the (6R,10S)-isomer of the corresponding ketal of 6,10,14-trimethyl-pentadecan-2-one
[3]is determined as ketone after hydrolysis of the ketal.

TABLE 2i

|  | 32 | 33 |
|---|---|---|
| Ketone to be hydrogenated | E-DHGA | |
| Ketal to be hydrogenated | E-DHGA-en | |
| Formula of Ir complex | III-F | III-F |
| Configuration of chiral Ir complex at * | (R) | (R) |
| conc.[1] [mol/L] | 1.0 | 0.9 |
| p$H_2$ [bar] | 50 | 50 |
| t [h] | 20 | 20 |
| S/C | 10'000 | 10'000 |
| Solvent | TFE | TFE |
| Assay yield [area-%] | 1 | 97 |
| Isomer-Distribution[3,4] | | |
| (R) [%] | n.d.[2] | 2.2 |
| (S) [%] | n.d.[2] | 97.8 |

Hydrogenation of E-DHGA and of E-DHGA-en. The effect of ketalization.
[1]conc. = mol ketone or ketal/L solvent
[2]n.d. = not determined (due to low assay yield)
[3](R) stands for the R-isomer, (S) stands for the S-isomer of the ethylene glycol ketal of 6,10-dimethylundecan-2-one
[4]is determined as ketone after hydrolysis of the ketal

TABLE 2j

|  | 34 | 35 | 36 | 37 |
|---|---|---|---|---|
| Ketone to be hydrogenated | Z-DHGA | | | |
| Ketal to be hydrogenated | | Z-DHGA-en | Z-DHGA-en | Z-DHGA-neo |
| Formula of Ir complex | III-F | III-F | III-F | III-F |
| Configuration of chiral Ir complex at * | (R) | (R) | (R) | (R) |
| conc.[1] [mol/L] | 1.0 | 0.2 | 0.2 | 0.2 |
| p$H_2$ [bar] | 50 | 25 | 25 | 25 |
| t [h] | 20 | 15 | 15 | 24 |
| S/C | 5'000 | 5'000 | 10'000 | 10'000 |
| Solvent | DCM | DCM | DCM | DCM |
| Assay yield [area-%] | 1 | 84 | 39 | 22 |
| Isomer-Distribution[3,4] | | | | |
| (R) [%] | n.d.[2] | 98.6 | 98.4 | 95 |
| (S) [%] | n.d.[2] | 1.4 | 1.6 | 5 |

Hydrogenation of Z-DHGA and of Z-DHGA-en and of Z-DHGA-neo. The effect of ketalization.
[1]conc. = mol ketone or ketal/L solvent (DCM = dichloromethane)
[2]n.d. = not determined (due to low assay yield)
[3](R) stands for the R-isomer, (S) stands for the S-isomer of the ethylene glycol ketal of 6,10-dimethylundecan-2-one
[4]is determined as ketone after hydrolysis of the ketal.

TABLE 2k

Hydrogenation of EE-FA and of FA-en. The effect of ketalization.

|  | 38 | 39 | 40 | 41 | 42 | 43 | 44 |
|---|---|---|---|---|---|---|---|
| Ketone to be hydrogenated | EE-FA | EE-FA |  |  |  | EE-FA |  |
| Ketal to be hydrogenated |  |  | EE-FA-en | EE-FA-en | EE-FA-en |  | EE-FA-en |
| Formula of Ir complex | III-F | III-F | III-F | III-F | III-F | III-F | III-F |
| Configuration of chiral Ir complex at * | (R) | (R) | (R) | (R) | (R) | (R) | (R) |
| conc.[1] [mol/L] | 0.2 | 0.2 | 0.2 | 0.2 | 0.2 | 0.2 | 0.2 |
| pH$_2$ [bar] | 50 | 25 | 25 | 25 | 25 | 25 | 50 |
| t [h] | 21 | 21 | 24 | 24 | 24 | 24 | 20 |
| S/C | 500 | 1'000 | 2'000 | 5'000 | 10'000 | 2'000 | 2'000 |
| Solvent | DCM | DCM | DCM | DCM | DCM | TFE | TFE |
| Assay yield [area-%] | 96 | 27 | 98 | 37 | 1 | 56 | 97 |
| Isomer-Distribution[3,4] |  |  |  |  |  |  |  |
| (SS) [%] | n.d.[2] | n.d.[2] | 96.3 | 96.3 | n.d.[2] | 94.4 | 96.5 |
| ((RR) + (SR)) [%] | n.d.[2] | n.d.[2] | 1.5 | 1.6 | n.d.[2] | 1.7 | 1.7 |
| (RS) [%] | n.d.[2] | n.d.[2] | 2.2 | 2.1 | n.d.[2] | 3.9 | 1.8 |

[1] conc. = mol ketone or ketal/L solvent (DCM = dichloromethane)
[2] n.d. = not determined
[3] (SS) stands for the (6S,10S)-isomer, (RR) stands for the (6R,10R)-isomer, (SR) stands for the (6S,10R)-isomer, (RS) stands for the (6R,10S)-isomer of the ethylene glycol ketal of 6,10,14-trimethyl-pentadecan-2-one
[4] is determined as ketone after hydrolysis of the ketal.

An autoclave was charged with 0.5 mmol (E)-2-(2,6-dimethylhepta-1,5-dien-1-yl)-5,5-dimethyl-1,3-dioxane or (E)-geranial, and with 4 g of dichloromethane and a solution of 2 mol % of the chiral iridium complex of formula (III-F) having the S-chirality at the centre indicated by * in said formula. The autoclave was closed and a pressure of 30 bar of molecular hydrogen was applied. The reaction mixture was stirred for 16 hours at 40° C. Afterwards the pressure was released and the solvent was removed. In case of hydrogenation of (E)-2-(2,6-dimethylhepta-1,5-dien-1-yl)-5,5-dimethyl-1,3-dioxane analysis by GC showed full conversion and a hydrogenated acetal purity of 71%, while only 2% product was observed in the (E)-geranial case.

Characterization Data (R)-2,2-dimethoxy-6,10-dimethylundecane (R-THGA-DM)

$^1$H NMR (300 MHz, CDCl$_3$): δ 0.848 (d, J=6.6 Hz, 3H) superimposed by 0.852 (d, J=6.6 Hz, 6H), 1.01-1.41 (m, 11H) superimposed by 1.25 (s, 3H), 1.44-1.61 (m, 3H), 3.16 (s, 6H) ppm.
$^{13}$C NMR (75 MHz, CDCl$_3$): δ 14.1 (1C), 19.6 (1C), 20.9 (1C), 21.7 (1C), 22.6 (1C), 22.7 (1C), 24.8 (1C), 27.9 (1C), 32.7 (1C), 36.8 (1C), 37.2 (1C), 37.4 (1C), 39.3 (1C), 47.9 (1C), 101.7 (1C) ppm.
MS (EI, m/z): No GC-MS was obtained due to decomposition on the column.
IR (cm$^{-1}$): 2951 (s), 2927 (m), 2870 (m), 2828 (m), 1723 (w), 1462 (m), 1377 (m), 1309 (w), 1256 (m), 1215 (m), 1194 (m), 1172 (m), 1111 (m), 1089 (m), 1053 (s), 972 (w), 934 (w), 920 (w), 855 (m), 815 (m), 736 (w), 618 (w).

(R)-2-(4,8-dimethylnonyl)-2,5,5-trimethyl-1,3-dioxane (R-THGA-neo)

$^1$H NMR (300 MHz, CDCl$_3$): δ 0.87 (d, J=6.6 Hz, 9H), 0.91 (s, 3H), 1.01 (s, 3H), 1.04-1.61 (m, 12H) superimposed by 1.36 (s, 3H), 1.61-1.74 (m, 2H), AB signal (δ$_A$=3.44, δ$_B$=3.54, J$_{AB}$=11.7 Hz, 4H) ppm.
$^{13}$C NMR (75 MHz, CDCl$_3$): δ 19.7 (1C), 20.4 (1C), 21.0 (1C), 22.56 (1C), 22.61 (1C), 22.71 (1C), 22.77 (1C), 24.8 (1C), 28.0 (1C), 30.0 (1C), 32.8 (1C), 37.3 (1C), 37.4 (1C), 38.2 (1C), 39.3 (1C), 70.3 (2C), 99.1 (1C) ppm.
MS (EI, m/z): 269 [(M-CH$_3$)$^+$, 65), 199 (8), 129 (100), 109 (8), 69 (32), 55 (10), 43 (25).
IR (cm$^{-1}$): 2953 (s), 2925 (s), 2868 (m), 1722 (w), 1464 (m), 1394 (m), 1371 (m), 1316 (w), 1258 (m), 1212 (m), 1161 (m), 1141 (m), 1111 (s), 1095 (s), 1043 (m), 1020 (m), 951 (m), 925 (m), 907 (m) 870 (m), 855 (m), 801 (m), 792 (m), 737 (m), 677 (w), 667 (w).

(R)-6,10-dimethyl-2,2-bis(2,2,2-trifluoroethoxy) undecane (R-THGA-tfe)

$^1$H NMR (300 MHz, CDCl$_3$): δ 0.88 (d, J=6.6 Hz, 6H), 0.87 (d, J=6.4 Hz, 3H), 1.03-1.23 (m, 5H), 1.39 (s, 3H), 1.38-1.40 (m, 6H), 1.46-1.71 (m, 3H), 3.73-3.94 (m, 4H).
$^{13}$C NMR (75 MHz, CDCl$_3$): δ 19.5 (1C), 21.39 (1C), 21.47 (1C), 22.58 (1C), 22.68 (1C), 24.7 (1C), 28.0 (1C), 32.6 (1C), 37.0 (1C), 37.19 (1C), 37.23 (1C), 39.3 (1C), 59.2 (q, $^2$J$_{C,F}$=32.5 Hz, 2C), 103.6 (1C), 124.1 (q, $^1$J$_{C,F}$=279.0 Hz, 2C).
MS (EI, m/z): 365 [(M-CH$_3$)$^+$, 1], 281 (2), 225 [(CF$_3$CH$_2$O)$_2$C—CH$_3$)$^+$, 100], 153 (8), 140 (6), 83 (CF$_3$CH$_2$$^+$, 6), 43 (7).
IR (cm$^{-1}$): 2955 (w), 2929 (w), 2872 (w), 1463 (w), 1419 (w), 1385 (w), 1281 (s), 1216 (w), 1156 (s), 1122 (m), 1082 (s), 972 (m), 892 (m), 861 (w), 737 (w), 679 (w), 663 (m).

(6R,10R)-2,2-dimethoxy-6,10,14-trimethylpentadecane (RR18-DM)

$^1$H NMR (300 MHz, CDCl$_3$): δ 0.83-0.89 (m, 12H), 0.98-1.45 (m, 21H), 1.46-1.65 (m, 3H), 3.18 (s, 6H).
$^{13}$C NMR (75 MHz, CDCl$_3$): δ 19.68 (1C), 19.73 (1C), 21.0 (1C), 21.7 (1C), 22.6 (1C), 22.7 (1C), 24.5 (1C), 24.8 (1C), 28.0 (1C), 32.72 (1C), 32.78 (1C), 36.8 (1C), 37.28 (1C), 37.33 (1C), 37.36 (1C), 37.41 (1C), 39.4 (1C), 48.0 (2C), 101.7 (1C) ppm.
IR (cm$^{-1}$): 2951 (s), 2926 (s), 2869 (s), 2828 (m), 1734 (w), 1723 (w), 1216 (w), 1463 (m), 1377 (s), 1308 (w), 1255 (m), 1215 (m), 1172 (s), 1105 (m), 1090 (m), 1054 (s), 971 (w), 933 (w), 860 (s), 815 (m), 736 (w) 618 (w).

2,5,5-trimethyl-2-((4R,8R)-4,8,12-trimethyltridecyl)-1,3-dioxane (RR18-neo)

$^1$H NMR (300 MHz, CDCl$_3$): δ 0.78-0.95 (m, 15H), 0.95-1.61 (m, 19H), superimposed by 1.01 (s, 3H), 1.36 (s, 3H), 1.63-1.74 (m, 2H), AB signal (δ$_A$=3.44, δ$_B$=3.55, J$_{AB}$=11.7 Hz, 4H) ppm.

$^{13}$C NMR (75 MHz, CDCl$_3$): δ 19.72 (1C), 19.74 (1C), 20.4 (1C), 20.9 (1C), 22.56 (1C), 22.62 (1C), 22.72 (1C), 22.77 (1C), 24.5 (1C), 24.8 (1C), 28.0 (1C), 30.0 (1C), 32.8 (1C), 32.8 (1C), 37.28 (1C), 37.35 (1C), 37.42 (2C), 38.2 (1C), 39.4 (1C), 70.3 (2C), 99.1 (1C) ppm.

MS (EI, m/z): 339 [(M-CH$_3$)$^+$, 83], 269 (5), 129 (100), 69 (21), 43 (18).

IR (cm$^{-1}$): 2952 (s), 2925 (s), 2867 (m), 1463 (m), 1394 (m), 1372 (m), 1258 (m), 1211 (m), 1189 (w), 1141 (w), 1100 (s), 1043 (m), 1020 (m), 951 (w), 925 (w), 907 (m), 858 (m), 792 (w), 737 (w), 677 (w).

(6R,10R)-6,10,14-trimethyl-2,2-bis(2,2,2-trifluoroethoxy)pentadecane (RR18-tfe)

$^1$H NMR (600 MHz, CDCl$_3$): δ 0.86 (d, J=6.6 Hz, 3H), 0.879 (d, J=6.6 Hz, 3H), 0.882 (d, J=6.6 Hz, 3H), 0.884 (d, J=6.6 Hz, 3H), 1.03-1.46 (m, 18H), superimposed by 1.40 (s, 3H), 1.54 (qqt, J=6.6, 6.6, 6.6 Hz, 1H), 1.60-1.70 (m, 2H), 3.77-3.90 (m, 4H) ppm.

$^{13}$C NMR (151 MHz, CDCl$_3$): δ 19.6 (1C), 19.7 (1C), 21.4 (1C), 21.5 (1C), 22.6 (1C), 22.7 (1C), 24.5 (1C), 24.8 (1C), 28.0 (1C), 32.6 (1C), 32.8 (1C), 37.0 (1C), 37.24 (1C), 37.30 (1C), 37.34 (1C), 37.43 (1C), 39.4 (1C), 59.2 (q, $^2$J$_{C,F}$=35.0 Hz, 2C), 103.6 (1C), 124.0 (q, $^1$J$_{C,F}$=277.0 Hz, 2C) ppm.

MS (EI, m/z): 435 [(M-CH$_3$)$^+$, 1], 351 (1), 250 (1), 225 [(CF$_3$CH$_2$O)$_2$C—CH$_3$)$^+$, 100], 153 (7), 140 (5), 83 (CF$_3$CH$_2$$^+$, 3), 43 (6).

IR (cm$^{-1}$): 2954 (m), 2927 (m), 2871 (w), 1463 (w), 1419 (w), 1384 (w), 1281 (s), 1215 (w), 1157 (s), 1123 (m), 1082 (s), 972 (s), 892 (m), 861 (w), 737 (w), 679 (w), 663 (m).

(R)-2-(2,6-dimethylheptyl)-5,5-dimethyl-1,3-dioxane (R-Tetrahydrocitral-neo)

$^1$H NMR (300 MHz, CDCl$_3$): δ 0.72 (s, 3H), 0.87 (d, J=6.6 Hz, 6H), 0.91 (d, J=6.4 Hz, 3H), 1.06-1.18 (m, 2H), 1.20 (s, 3H), 1.22-1.78 (m, 8H), 3.43 (dd, J=11.2, 1.4 Hz, 2H), 3.61 (d, J=11.2 Hz, 2H), 4.48 (t, J=5.2 Hz, 1H) ppm.

$^{13}$C NMR (75 MHz, CDCl$_3$): δ 19.7 (1C), 21.9 (1C), 22.6 (1C), 22.7 (1C), 23.1 (1C), 24.5 (1C), 27.9 (1C), 28.6 (1C), 29.7 (1C), 30.1 (1C), 37.5 (1C), 39.2 (1C), 42.1 (1C), 77.3 (1C), 101.4 (1C) ppm.

MS (EI, m/z): 241.3 [(M-H)$^+$, 10], 200 (1), 155 (4), 130 (4), 115 (100), 69 (35), 56 (21), 41 (19).

IR (cm$^{-1}$): 2953 (s), 2924 (s), 2854 (m), 1744 (w), 1645 (w), 1461 (m), 1406 (w), 1393 (w), 1378 (w), 1284 (m), 1252 (w), 1230 (w), 1162 (s), 1122 (s), 1083 (m), 1044 (w), 1017 (w), 974 (m), 932 (w), 921 (w), 890 (w), 837 (w), 735 (w), 666 (w).

Experiment E4

Hydrolysis of Hydrogenated Ketals/Acetals

After the asymmetric hydrogenation of ketals or acetals as shown in experiment E3, the hydrogenated ketals or acetals obtained were hydrolysed to the ketone or aldehyde.

Method 1—Neopentyl Ketals, Dimethyl Ketals from Asymmetric Hydrogenation Reactions in Dichloromethane A sample of the reaction mixture from the asymmetric hydrogenation reaction (1-2 ml) was stirred with an equal volume of 1M aqueous solution of hydrochloric acid at room temperature for 1 hour. Dichloromethane (2 ml) was added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.

Method 2—Ethylene Glycol Ketals, Bis(Trifluoroethanol) Ketals and Dimethyl Ketals from Asymmetric Hydrogenation Reactions in Trifluoroethanol A sample of the reaction mixture from the asymmetric hydrogenation reaction (1-2 ml) was stirred with 0.5 ml of a solution of 9:1:0.2 (by volume) methanol:water:trifluoroacetic acid at 40° C. for 1 hour. Dichloromethane (2 ml) and water (2 ml) were added and the layers were separated. The aqueous layer was washed with dichloromethane (2 ml) twice. The combined organic layers were evaporated under reduced pressure to yield the ketone as a colourless to pale-yellow oil. The crude ketone was then analysed for purity and isomer ratio.

Method 3—Acetals

A sample of the hydrogenated acetal (30 mg) ((R)-2-(2,6-dimethylheptyl)-5,5-dimethyl-1,3-dioxane (R-Tetrahydrocitral-neo)) was dissolved in formic acid (3 mL) under argon, treated with sodium formate (50 mg) and heated to 70° C. for 1 h. After cooling, the reaction was diluted with water (10 mL) and EtOAc (20 mL). The organic phase was washed with brine (5 mL), dried over MgSO$_4$ and concentrated. (R)-3,7-dimethyloctanal (R-Tetrahydrocitral) was analyzed for its stereoisomer ratio.

Experiment E5

Asymmetric Hydrogenations of Ketals in the Presence of Additives

An autoclave vessel was charged under nitrogen with chiral iridium complex of formula (III-F) of the R configuration at the chiral centre marked by *, the ketal in an amount (conc.) as indicated in tables 3a to f, solvent as indicated in tables 3a to f and an additive as indicated in tables 3a to f. The reactive vessel was closed and pressurized with molecular hydrogen to the pressure (pH$_2$) indicated in tables 3a to f. The reaction mixture was stirred at room temperature for the time (t) as indicated in tables 3a to f under hydrogen. Then the pressure was released and the assay yield and the stereoisomer distribution of the fully hydrogenated product were determined. In case of ketals the assay yield and the stereoisomer stereoisomer distribution have been determined after the hydrolysis of the ketal by acid as indicated in experiment E4. The catalyst loading (S/C) is defined as mmol ketal ("substrate")/mmol chiral iridium complex.

Preparation of Additives
  MAO/TFE: A 1.6 M MAO (MAO: methylaluminoxane solution in toluene (0.64 mL) was quenched with 2,2,2-trifluorethanol (TFE) (3.1 mmol), leading to small excess of free TFE.
  EAO/TFE: A 10 wt % EAO (EAO: ethylaluminoxane solution in toluene (1 mmol) was quenched with TFE (3.2 mmol), leading to small excess of free TFE.

TMA/TFE: A 2 M TMA (TMA: trimethylaluminum (Al(CH$_3$)$_3$)) solution in heptane (1 mmol) was quenched with TFE (3.1 mmol), leading to small excess of free TFE.

TEA/TFE: A 2 M TEA (TEA: triethylaluminum (Al(CH$_2$CH$_3$)$_3$)) solution in heptane (1 mmol) was quenched with TFE (3.1 mmol), leading to small excess of free TFE.

TMA/BHT/TFE: A 2 M TMA solution in heptane (1 mmol) was quenched with 2,6-di-tert-butyl-4-methylphenol (BHT) (2 mmol) and subsequently with TFE (3.1 mmol), leading to small excess of free TFE.

Ti(OCH$_2$CF$_3$)$_4$: Tetraisopropyl orthotitanate (8.1 mmol) was dissolved in 2,2,2-trifluoroethanol at 50° C. Removal of the solvent gave Ti(OCH$_2$CF$_3$)$_4$ as a white residue which was isolated and identified to be Ti(OCH$_2$CF$_3$)$_4$.

These additives were freshly prepared and used either as a heterogeneous mixture at room temperature or homogeneous by heating to a temperature between 50° and 70° C.

The additives tetraisopropyl orthotitanate (Ti(OiPr)$_4$), triisopropylborate (B(OiPr)$_3$), sodium tetrakis[3,5-bis(trifluoromethyl)phenyl]borate (NaBAr$_F$) and triethyl borane (TEB) (1 M solution in hexane) are commercially available and were used as received.

Triflic acid was introduced in the hydrogenation experiments as a freshly prepared 0.1 M solution in dichloromethane.

TABLE 3a

|  | 45 | 46 | 47 | 48 | 49 |
|---|---|---|---|---|---|
| Ketal to be hydrogenated | E-DHGA-en | E-DHGA-en | E-DHGA-en | E-DHGA-en | E-DHGA-en |
| conc.[1] [mol/L] | 0.2 | 0.7 | 0.2 | 2.3 | Neat |
| S/C | 10'000 | 30'000 | 20'000 | 20'000 | 20'000 |
| Solvent | DCM | DCM | DCM | hexane | — |
| Additive | — | MAO/TFE | TMA/TFE | TEB | B(OiPr)$_3$ |
| Additive concentration [mol-%][2] | — | 10 | 2 | 5 | 10 |
| Assay yield [area-%] | 68 | 99 | 99 | 83 | 97 |
| Isomer-Distribution[3,4] | | | | | |
| (R) [%] | 5 | 3 | 2 | 3.4 | 2.6 |
| (S) [%] | 95 | 97 | 98 | 96.6 | 97.4 |

Hydrogenation of E-DHGA-en at pressure of molecular hydrogen (pH$_2$) of 50 bar and stirring at room temperature during 20 hours. The effect of the additives.
[1]conc. = mol ketal/L solvent
[2]relative to the molar amount of E-DHGA-en
[3](R) stands for the R-isomer, (S) stands for the S-isomer of the ethylene glycol ketal of 6,10-dimethylundecan-2-one
[4]is determined as ketone after hydrolysis of the ketal TABLE 3b Hydrogenation of different ketals of Z-DHGA at pressure of molecular hydrogen (pH$_2$) of 50 bar and stirring at room temperature during 20 hours. The effect of the additives.

|  | 50 | 51 | 52 | 53 | 54 | 55 |
|---|---|---|---|---|---|---|
| Ketal to be hydrogenated | Z-DHGA-en | Z-DHGA-en | Z-DHGA-en | Z-DHGA-en | Z-DHGA-neo | Z-DHGA-neo |
| conc.[1] [mol/L] | 0.2 | 0.2 | 0.2 | 0.2 | 0.2 | 0.2 |
| S/C | 5'000 | 10'000 | 10'000 | 52'000 | 20'000 | 20'000 |
| Solvent[3] | DCM | DCM | TFE | TFE | TFE | TFE |
| Additive | — | — | NaBAr$_F$ | TMA[4] | — | TMA[4] |
| Additive concentration [mol-%][2] | — | — | 0.014 | 100 | — | 10 |
| Assay yield [area-%] | 84 | 39 | 46 | 93 | 4 | 63 |
| Isomer-Distribution[5,6] | | | | | | |
| (R) [%] | 98.6 | 98.4 | 97.5 | 98.1 | 85.4 | 98.8 |
| (S) [%] | 1.4 | 1.6 | 2.5 | 1.9 | 14.6 | 1.2 |

[1]conc. = mol ketal/L solvent
[2]relative to the molar amount of ketal of Z-DHGA
[3]TFE = 2,2,2-trifluoroethanol; DCM = dichloromethane
[4]TMA is quenched by adding into the solvent TFE
[5](R) stands for the R-isomer, (S) stands for the S-isomer of the corresponding ketal of 6,10-dimethylundecan-2-one
[6]is determined as ketone after hydrolysis of the ketal TABLE 3c

|  | 56 | 57 | 58 | 59 | 60 |
|---|---|---|---|---|---|
| Ketal to be hydrogenated | EE-FA-en | EE-FA-en | EE-FA-en | EE-FA-en | EE-FA-en |
| conc.[1] [mol/L] | 0.2 | 0.2 | 0.2 | 0.2 | 0.2 |
| S/C | 5'000 | 5'000 | 5'000 | 5'000 | 5'000 |
| Solvent | DCM | DCM | TFE | TFE | TFE |
| Additive | — | TMA/TFE | — | Triflic acid | Ti(OiPr)$_4$ |
| Additive concentration [mol-%][2] | — | 10 | — | 0.12 | 13 |
| Pressure of H$_2$ [bar] | 25 | 25 | 25 | 25 | 25 |
| Time of hydrogenation: t [h] | 24 | 24 | 20 | 20 | 24 |
| Assay yield [area-%] | 37 | 72 | 2 | 85 | 94 |
| Isomer-Distribution[3,4] | | | | | |
| (RS) [%] | 2.1 | 4 | n.d.[5] | 4 | 2 |
| ((RR) + (SR)) [%] | 1.6 | 2 | n.d.[5] | 3 | 2 |
| (SS) [%] | 96.3 | 94 | n.d.[5] | 93 | 96 |

Hydrogenation of EE-FA-en stirring at room temperature. The effect of the additives
[1]conc. = mol ketal/L solvent
[2]relative to the molar amount of EE-FA-en.
[3](SS) stands for the (6S,10S)-isomer, (RR) stands for the (6R,10R)-isomer, (SR) stands for the (6S,10R)-isomer, (RS) stands for the (6R,10S)-isomer of the ethylene glycol ketal of 6,10,14-trimethyl-pentadecan-2-one
[4]is determined as ketone after hydrolysis of the ketal.
[5]n.d. = not determined TABLE 3d

|  | 61 | 62 | 63 | 64 | 65 |
|---|---|---|---|---|---|
| Ketal to be hydrogenated | EE-FA-en | EE-FA-en | EE-FA-en | EE-FA-en | EE-FA-en |
| conc.[1] [mol/L] | neat | neat | neat | 2 | 1 |
| S/C | 10'000 | 20'000 | 30'000 | 20'000 | 20'000 |
| Solvent | — | — | — | heptane | heptane |
| Additive | — | MAO/TFE | MAO/TFE | EAO/TFE | MAO/TFE |
| Additive concentration [mol-%][2] | — | 10 | 10 | 10 | 10 |
| Pressure of $H_2$ [bar] | 50 | 50 | 50 | 50 | 50 |
| Time of hydrogenation: t [h] | 20 | 20 | 20 | 20 | 20 |
| Assay yield [area-%] | 3 | 99 | 92 | 95 | 99 |
| Isomer-Distribution[3,4] |  |  |  |  |  |
| (RS) [%] | n.d.[5] | 2.6 | 2.7 | n.d.[5] | 2.5 |
| ((RR) + (SR)) [%] | n.d.[5] | 1.7 | 1.7 | n.d.[5] | 1.4 |
| (SS) [%] | n.d.[5] | 95.7 | 95.6 | n.d.[5] | 96.1 |

Hydrogenation of EE-FA-en stirring at room temperature. The effect of the additives.
[1]conc. = mol ketal/L solvent
[2]relative to the molar amount of EE-FA-en.
[3](SS) stands for the (6S,10S)-isomer, (RR) stands for the (6R,10R)-isomer, (SR) stands for the (6S,10R)-isomer, (RS) stands for the ethylene glycol ketal of (6R,10S)-isomer of 6,10,14-trimethylpentadecan-2-one.
[4]is determined as ketone after hydrolysis of the ketal
[5]n.d. = not determined TABLE 3e

|  | 66 | 67 | 68 | 69 |
|---|---|---|---|---|
| Ketal to be hydrogenated | EE-FA-en | EE-FA-en | EE-FA-en | EE-FA-en |
| conc.[1] [mol/L] | 4 | 2.5 | 2.5 | 1.8 |
| S/C | 10'000 | 10'000 | 10'000 | 10'000 |
| Solvent | heptane | heptane | heptane | heptane |
| Additive | TMA/BHT/TFE | TMA/TFE | TEA/TFE | TEB |
| Additive concentration [mol-%][2] | 5 | 2 | 2 | 10 |
| Pressure of $H_2$ [bar] | 50 | 50 | 50 | 50 |
| Time of hydrogenation: t [h] | 20 | 20 | 20 | 20 |
| Assay yield [area-%] | 97 | 99 | 95 | 98 |
| Isomer-Distribution[3,4] |  |  |  |  |
| (RS) [%] | 3.0 | 2.8 | 2.6 | 2.6 |
| ((RR) + (SR)) [%] | 1.7 | 1.6 | 1.5 | 1.5 |
| (SS) [%] | 95.3 | 95.6 | 95.9 | 95.9 |

Hydrogenation of EE-FA-en stirring at room temperature. The effect of additives.
[1]conc. = mol ketal/L solvent
[2]relative to molar amount of EE-FA-en.
[3](SS) stands for the (6S,10S)-isomer, (RR) stands for the (6R,10R)-isomer, (SR) stands for the (6S,10R)-isomer, (RS) stands for the (6R,10S)-isomer of the ethylene glycol ketal of 6,10,14-trimethylpentadecan-2-one.
[4]is determined as ketone after hydrolysis of the ketal TABLE 3f

|  | 70 | 71 | 72 |
|---|---|---|---|
| Ketal to be hydrogenated | EE-DHFA-en | EE-DHFA-en | EE-DHFA-en |
| conc.[1] [mol/L] | neat | 1.8 | Neat |
| S/C | 10'000 | 10'000 | 30'000 |
| Solvent | — | heptane | — |
| Additive | — | TMA/TFE | MAO/TFE |
| Additive concentration [mol-%][2] | — | 2 | 10 |
| Assay yield [area-%] | 27 | 85 | 97 |
| Isomer-Distribution[3,4] |  |  |  |
| (RS) [%] | 2.3 | 2.3 | 2.3 |
| ((RR) + (SR)) [%] | 6.1 | 5.9 | 6 |
| (SS) [%] | 91.6 | 91.8 | 91.7 |

Hydrogenation of EE-DHFA-en at pressure of molecular hydrogen (pH$_2$) of 50 bar and stirring at room temperature during 20 hours. The effect of the additives.
[1]conc. = mol ketal/L solvent
[2]relative to the molar amount of EE-DHFA-en.
[3](SS) stands for the (6S,10S)-isomer, (RR) stands for the (6R,10R)-isomer, (SR) stands for the (6S,10R)-isomer, (RS) stands for the (6R,10S)-isomer of the ethylene glycol ketal of 6,10,14-trimethylpentadecan-2-one.
[4]is determined as ketone after hydrolysis of the ketal

The invention claimed is:

1. A process for the asymmetric hydrogenation of a ketal of an unsaturated ketone or an acetal of an unsaturated aldehyde which comprises subjecting a ketal of an unsaturated ketone or an acetal of an unsaturated aldehyde to hydrogenation conditions with molecular hydrogen in the presence of at least one chiral iridium complex to yield a ketal or acetal having at least one stereogenic carbon centre, wherein the unsaturated ketone or unsaturated aldehyde is a ketone or an aldehyde having a carbon-carbon double bond in the γ, δ-position to the C=O group.

2. The process according to claim 1, wherein the ketal or acetal is obtained from a reaction of a corresponding unsaturated ketone or a corresponding unsaturated aldehyde and an alcohol.

3. The process according to claim 1, wherein the unsaturated ketone or unsaturated aldehyde is an unsaturated ketone or unsaturated aldehyde according to formula (I) or formula (II):

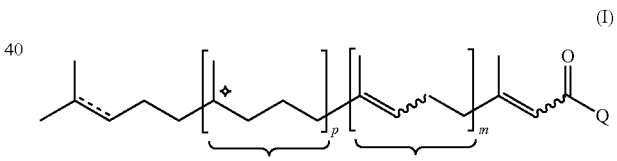

(I)

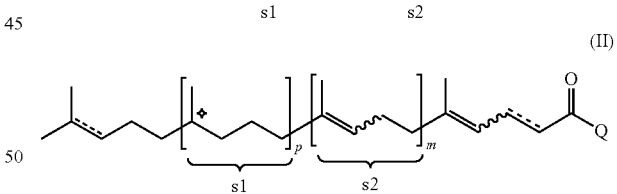

(II)

wherein Q stands for H or CH$_3$ and m and p stand independently from each other for a value of 0 to 3 with the proviso that the sum of m and p is 0 to 3, and wherein a wavy line represents a carbon-carbon bond which is linked to the adjacent carbon-carbon double bond so as to have said carbon-carbon double bond either in the Z or in the E-configuration and where the substructures in formula (I) and formula (II) represented by S1 and s2 can be in any sequence; and wherein the double bond having dotted lines ( ══ ) in formula (I) and formula (II) represent either a single carbon-carbon bond or a double carbon-carbon bond; and wherein ✧ represents a stereogenic centre.

4. The process according to claim 1, wherein the chiral iridium complex is an iridium complex having ligands bound to an iridium central atom, and wherein exactly one of the ligands is an organic ligand bearing a stereogenic centre.

5. The process according to claim 3, wherein the chiral iridium complex is a chiral iridium complex of formula (III-0):

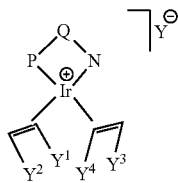

(III-0)

wherein
P-Q-N stands for a chelating organic ligand comprising a stereogenic centre or has planar or axial chirality and has a nitrogen and phosphorous atom as binding site to the iridium centre of the complex;
$Y^1$, $Y^2$, $Y^3$ and $Y^4$ are independently from each other are hydrogen atoms, $C_{1-12}$-alkyl, $C_{5-10}$-cycloalkyl, or aromatic group; or at least two of $Y^1$, $Y^2$, $Y^3$ and $Y^4$ form together at least a two-valent bridged group of at least 2 carbon atoms; and
$Y^\ominus$ is an anion selected from the group consisting of halide, $PF_6^-$, $SbF_6^-$, tetra(3,5-bis(trifluoromethyl)phenyl)borate ($BAr_F^-$), $BF_4^-$, perfluorinated sulfonate, $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$.

6. The process according to claim 1, wherein the chiral iridium complex has the formula (III):

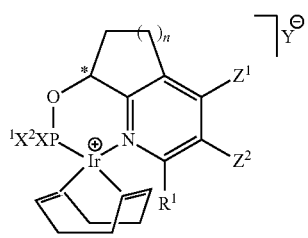

(III)

wherein
n is 1 or 2 or 3, preferred 1 or 2;
$X^1$ and $X^2$ are independently from each other hydrogen atoms, $C_{1-4}$-alkyl, $C_{5-7}$-cycloalkyl, adamantyl, phenyl optionally substituted with one to three $C_{1-5}$-alkyl, $C_{1-4}$-alkoxy, $C_{1-4}$-perfluoroalkyl groups and/or one to five halogen atoms, benzyl, 1-naphthyl, 2-naphthyl, 2-furyl or ferrocenyl;
$Z^1$ and $Z^2$ are independently from each other hydrogen atoms, $C_{1-5}$-alkyl or $C_{1-5}$-alkoxy groups; or $Z^1$ and $Z^2$ stand together for a bridging group forming a 5 to 6 membered ring;
$Y^\ominus$ is an anion selected from the group consisting of halide, $PF_6^-$, $SbF_6^-$, tetra(3,5-bis(trifluoromethyl)phenyl)borate($BAr_F^-$), $BF_4^-$, perfluorinated sulfonate, $ClO_4^-$, $Al(OC_6F_5)_4^-$, $Al(OC(CF_3)_3)_4^-$, $N(SO_2CF_3)_2^-N(SO_2C_4F_9)_2^-$ and $B(C_6F_5)_4^-$;

$R^1$ represents either phenyl or o-tolyl or m-tolyl or p-tolyl or a group of formula (IVa), formula (IVb) or formula (IVc):

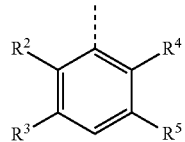

(IVa)

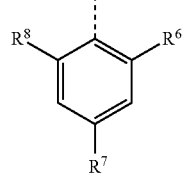

(IVb)

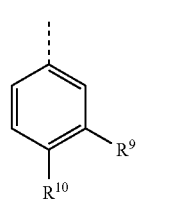

(IVc)

wherein $R^2$ and $R^3$ represent either both H or a $C_1$-$C_4$-alkyl group or a halogenated $C_1$-$C_4$-alkyl group or represent a divalent group forming together a 6-membered cycloaliphatic or an aromatic ring which optionally is substituted by halogens atoms or by $C_1$-$C_4$-alkyl groups or by $C_1$-$C_4$-alkoxy groups
$R^4$ and $R^5$ represent either both H or a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups;
each of $R^6$, $R^7$ and $R^8$ represents $C_1$-$C_4$-alkyl group or a halogenated $C_1$-$C_4$-alkyl group;
$R^9$ and $R^{19}$ represent either both H, a $C_1$-$C_4$-alkyl group or a halogenated $C_1$-$C_4$-alkyl group or a divalent group forming together a 6-membered cycloaliphatic or an aromatic ring which optionally is substituted by halogens atoms or by $C_1$-$C_4$-alkyl groups or by $C_1$-$C_4$-alkoxy groups; and
wherein * represents a stereogenic centre of the complex of formula (III).

7. The process according to claim 1, wherein the chiral iridium complex is present during the hydrogenation in an amount from 0.0001 to 5 mol-%, based on the amount of the acetal or ketal.

8. The process according to claim 1, wherein the process comprises performing hydrogenation in the presence of an additive selected from the group consisting of organic sulfonic acids, transition metal salts of organic sulfonic acids, metal alkoxides, aluminoxanes, alkyl aluminoxanes and $B(R)_{(3-v)}(OZ)_v$; wherein
v stands for 0, 1, 2 or 3;
R stands for F, a $C_{1-6}$-alkyl, a halogenated $C_{1-6}$-alkyl, an aryl or halogenated aryl group; and
Z stands a $C_{1-6}$-alkyl, a halogenated $C_{1-6}$-alkyl, an aryl or halogenated aryl group.

9. The process according to claim 8, wherein the additive is selected from the group consisting of triflic acid, alkyl aluminoxanes, tetra alkoxy titanates, tri-isopropylborate, triethylborane and $BF_3$.

10. The process according to claim 1, wherein the process comprises conducting hydrogenation in the presence of a halogenated alcohol.

11. The process according to claim 2, wherein the alcohol is a monol or a diol.

12. The process according to claim 2, wherein the alcohol is a halogenated $C_1$-$C_8$-alkyl alcohol.

13. The process according to claim 2, wherein the alcohol is selected from the group consisting of ethane-1,2-diol, propane-1,2-diol, propane-1,3-diol, butane-1,4-diol, butane-1,3-diol, butane-1,2-diol, butane-2,3-diol, 2-methylpropane-1,2-diol, 2-methylpropane-1,3-diol, 2,2-dimethylpropane-1,3-diol, 1,2-dimethylpropane-1,3-diol, 3-methylpentane-2,4-diol and 2-(hydroxymethyl)cyclohexanol, benzene-1,2-diol and cyclohexane-1,2-diol.

14. The process according to claim 4, wherein organic ligand bearing a stereogenic centre is a chelating ligand bearing a stereogenic centre.

15. The process according to claim 5, wherein $Y^{\ominus}$ is $F_3C$—$SO_3^-$ or $F_9C_4$—$SO_3^-$.

16. The process according to claim 6, wherein $Y^{\ominus}$ is $F_3C$—$SO_3^-$ or $F_9C_4$—$SO_3^-$.

17. The process according to claim 7, wherein the chiral iridium complex is present during the hydrogenation in an amount from about 0.001 to about 2 mol-%, based on the amount of the acetal or ketal.

18. The process according to claim 7, wherein the chiral iridium complex is present during the hydrogenation in an amount from about 0.001 to about 1 mol-%, based on the amount of the acetal or ketal.

19. The process according to claim 7, wherein the chiral iridium complex is present during the hydrogenation in an amount from 0.001 to 0.1 mol-%, based on the amount of the acetal or ketal.

20. The process according to claim 9, wherein the additive is methyl aluminoxane or ethyl aluminoxane.

21. The process according to claim 9, wherein the additive is a $BF_3$ etherate.

22. The process according to claim 10, wherein the halogenated alcohol is 2,2,2-trifluoroethanol.

23. A process of manufacturing aldehydes or ketones having at least one stereogenic carbon centre comprising the steps of:
   α) forming a ketal from an unsaturated ketone or an acetal of an unsaturated aldehyde and an alcohol or by treating a ketone or an aldehyde with ortho-esters or by trans-ketalization or by trans-acetalization;
   β) performing a process of asymmetric hydrogenation according to claim 1 yielding a ketal or acetal having at least one stereogenic carbon centre;
   γ) hydrolysing the ketal or acetal having at least one stereogenic carbon centre formed by step β).

24. A composition comprising:
   i) at least one ketal of an unsaturated ketone or at least one acetal of an unsaturated aldehyde;
   ii) at least one chiral iridium complex.

25. The composition according to claim 24, wherein the composition further comprises a halogenated alcohol and/or an additive selected from the group consisting of organic sulfonic acids, transition metal salts of organic sulfonic acids, metal alkoxides, aluminoxanes, alkyl aluminoxanes and $B(R)_{(3-v)}(OZ)_v$;
wherein
v stands for 0, 1, 2 or 3 and
R stands for F, a $C_{1-6}$-alkyl, a halogenated $C_{1-6}$-alkyl, an aryl or halogenated aryl group; and
Z stands a $C_{1-6}$-alkyl, a halogenated $C_{1-6}$-alkyl, an aryl or halogenated aryl group.

* * * * *